United States Patent
Multhoff

(10) Patent No.: US 11,460,472 B2
(45) Date of Patent: Oct. 4, 2022

(54) QUANTITATIVE ASSAY FOR HEAT SHOCK PROTEINS 70 (HSP70) PROTEIN IN BODY FLUIDS

(71) Applicant: multimmune GmbH, Munich (DE)

(72) Inventor: Gabriele Multhoff, Munich (DE)

(73) Assignee: MULTIMMUNE GMBH, Munich (DE)

(*) Notice: Subject to any disclaimer, the term of this patent is extended or adjusted under 35 U.S.C. 154(b) by 0 days.

(21) Appl. No.: 15/546,394

(22) PCT Filed: Jan. 27, 2016

(86) PCT No.: PCT/EP2016/051700
§ 371 (c)(1),
(2) Date: Jul. 26, 2017

(87) PCT Pub. No.: WO2016/120325
PCT Pub. Date: Aug. 4, 2016

(65) Prior Publication Data
US 2018/0017567 A1 Jan. 18, 2018

(30) Foreign Application Priority Data
Jan. 27, 2015 (EP) .................................. 15152725

(51) Int. Cl.
G01N 33/53 (2006.01)
G01N 33/574 (2006.01)
G01N 33/577 (2006.01)
G01N 33/68 (2006.01)

(52) U.S. Cl.
CPC ..... *G01N 33/57488* (2013.01); *G01N 33/574* (2013.01); *G01N 33/577* (2013.01); *G01N 33/6896* (2013.01); *G01N 2800/285* (2013.01); *G01N 2800/52* (2013.01)

(58) Field of Classification Search
CPC .......... G01N 33/57488; G01N 33/574; G01N 33/577; G01N 33/6896; G01N 2800/285; G01N 2800/52; G01N 2470/00; G01N 2470/04; G01N 2470/06; G01N 2470/10; G01N 2470/12
See application file for complete search history.

(56) References Cited

U.S. PATENT DOCUMENTS

2012/0087931 A1* 4/2012 Multhoff ................ C07K 16/18
424/174.1

FOREIGN PATENT DOCUMENTS

| EP | 2 141 499 A1 | 1/2010 |
|----|-----|-----|
| WO | WO 2005/054295 A2 | 6/2005 |
| WO | WO 2005/054868 A1 | 6/2005 |

OTHER PUBLICATIONS

Hurvitz et al (Radiotherapy and oncology 2010;vol. 95;p. 350-358).*
Gastpar,(Cancer Res 2005; 65 (12) p. 5238-5247).*
Friedrich et al (Protein Engineering, Design and selection, 2010; vol. 23 No. 4,pp. 161-168).*
Abeam Polyclonal anti-Hsp70 (1998;retrieved from https://www.abcam.com/hsp70-antibody-ab31010.html#top-133).*
Thermofisher ELISA Guide (2005, http://www.kpl.com/docs/techdocs/KPL%20ELISA%20Technical%20Guide.pdf.*
Njemi et al (Journal of immunological Methods, 2005; 306, p. 176-182).*
Applichem Immunoassay Buffer (2008;retrieved from https://www.dia-m.ru/applichem/brochures/Immunoassay_en.pdf).*
International Search Report and Written Opinion prepared by the European Patent Office dated Mar. 7, 2016, for International Application No. PCT/EP2016/051700.
Gehrmann et al: "Hsp70-a biomarker for tumor detection and monitoring of outcome of radiation therapy in patients with squamous cell carcinoma of the head and neck." Radiation Oncology, Biomed Central Ltd, Lo, vol. 9, No. 1, Jun. 9, 2014 (Jun. 9, 2014), p. 131.
L. Friedrich et al: "Bacterial production and functional characterization of the Fab fragment of the murine IgG1/monoclonal antibody cmHsp70.1, a reagent for tumour diagnostics", Protein Engineering Design and Selection, vol. 23, No. 4, Feb. 1, 2010 (Feb. 1, 2010), pp. 161-168.
Kirstin A. Zettlitz et al: "Humanization of a Mouse Monoclonal Antibody Directed Against a Cell Surface-Exposed Epitope of Membrane-Associated Heat Shock Protein 70 (Hsp70)", Molecular Biotechnology, vol. 46, No. 3, Jun. 17, 2010 (Jun. 17, 2010), pp. 265-278.
Xiaomin Zhang et al: "Plasma levels of Hsp70 and anti-Hsp70 antibody predict risk of acute coronary syndrome", Cell Stress and Chaperones, vol. 15, No. 5, Mar. 19, 2010 (Mar. 19, 2010), pp. 675-686.
G.I. Lancaster et al: "Exosome-dependent Trafficking of HSP70: A Novel Secretory Pathway for Cellular Stress Proteins", Journal of Biological Chemistry, vol. 280, No. 24, Jun. 17, 2005 (Jun. 17, 2005), pp. 23349-23355.
International Preliminary Report on Patentability for International (PCT) Patent Application No. PCT/EP2016/051700, dated Aug. 10, 2017, 10 pages.
Breuninger et al. "Quantitative Analysis of Liposomal Heat Shock Protein 70 (Hsp70) in the Blood of Tumor Patients Using a Novel LipHsp70 ELISA," Journal of Clinical & Cellular Immunology, 2014, vol. 5, No. 5, 1000264, 10 pages.
Bayer et al. "Validation of Heat Shock Protein 70 as a Tumor-Specific Biomarker for Monitoring the Outcome of Radiation Therapy in Tumor Mouse Models," International Journal of Radiation Oncology, Biology, Physics, 2014, vol. 88, No. 3, pp. 694-700.

* cited by examiner

*Primary Examiner* — Carmencita M Belei
(74) *Attorney, Agent, or Firm* — Sheridan Ross P.C.

(57) ABSTRACT

Provided is a novel kit and assay for free and lipid-bound (exosomal) Hsp70. In particular, an ELISA is described for determining the level of Hsp70 in sample derived from a body fluid of a subject, characterized in that the level of Hsp70 is determined by an anti-Hsp70 antibody.

6 Claims, 11 Drawing Sheets

QUANTITATIVE ASSAY FOR HEAT SHOCK PROTEINS 70 (HSP70) PROTEIN IN BODY FLUIDS

CROSS REFERENCE TO RELATED APPLICATIONS

This application is a national stage application under 35 U.S.C. 371 and claims the benefit of PCT Application No. PCT/EP2016/051700 having an international filing date of 27 Jan. 2016, which designated the United States, which PCT application claimed the benefit of European Patent Application No. 15152725.6 filed 27 Jan. 2015, the disclosure of each of which are incorporated herein by reference.

FIELD OF THE INVENTION

The present invention relates to a method for the assessment of blood-borne biomarkers for the detection and diagnosis of disorders and diseases associated with heat shock protein 70 (Hsp70) such as tumors, including, but not limited to, human head and neck cancer, lung cancer, colorectal carcinoma, pancreatic cancer, glioblastoma and hematological malignancies as well as infectious diseases or inflammatory disorders such as multiple sclerosis (MS). In accordance with the present invention, the practice of the detection and diagnosis of tumors, infections or inflammation is indicated by the presence and localization of certain markers in diseased tissue or cells. In particular, the present invention relates to a method of diagnosing a disease or condition associated with free and lipid-bound (exosomal) Hsp70, for example lipid-associated Hsp70 in exosomes and in the plasma membrane of living tumor cells, which in accordance with the present invention is reflected by an increased levels of lipid-bound (exosomal) Hsp70 and a specific conformational epitope of lipid-bound (exosomal) Hsp70, respectively, in a body fluid, in particular plasma or serum of the subject affected with the disease or condition.

This finding led to the development of a novel method for assaying free and lipid-bound (exosomal) heat shock protein 70 (Hsp70) in a sample derived from a body fluid of a subject, preferably an anti-Hsp70 antibody comprising determining the level of free and lipid-bound (exosomal) Hsp70 in a sample derived from a body fluid, preferably plasma or serum of the subject, wherein the increased level of Hsp70 in the sample of the subject compared to a control indicates the presence of or provides the opportunity to monitor a tumor, respectively, wherein the method is characterized in that the level of free and lipid-bound (exosomal) heat shock protein 70 (Hsp70) is determined by way of detecting a particular conformational epitope of Hsp70.

BACKGROUND OF THE INVENTION

Heat Shock Proteins (Hsp) are molecular chaperones that play a key role in maintaining protein homeostasis and transport. Heat shock proteins with a molecular weight of approximately 70 kDa (Hsp70) are involved in assisting protein folding, preventing protein aggregation and transporting proteins across membranes [1, 2]. The heat shock cognate protein 70 (Hsc70) and the major stress-inducible heat shock protein 70 (Hsp70), which are present in all nucleated eukaryotic cells, show a high sequence homology of 86% [3]. Following a variety of different stress stimuli, the synthesis of Hsc70 is moderately [4], while that of Hsp70 is highly upregulated in normal cells [1]. In contrast to normal cells, tumor cells frequently overexpress inducible Hsp70 already under physiological conditions [5] and present it on their plasma membrane [6]. Since Hsp70 on the membrane of tumor cells could not be removed with high salt, acid or basic washes [7, 8], experimental evidence given that Hsp70 is not merely associated with membrane proteins [9] but rather interacts with the lipid bilayer of the plasma membrane. Lipid profiling revealed that stress-inducible Hsp70 interacts with the tumor-specific lipid component globoyltriaosylceramide [7] under non-stressed conditions and with phosphatidylserine [8, 10] following stress with high prevalence.

An Hsp70 membrane-positivity has been found in a large variety of different tumor entities such as head and neck, lung, colorectal, pancreas, breast carcinomas and hematological malignancies, but not on the corresponding normal tissues [13, 14]. In addition, Hsp70 membrane-positive tumor cells but not their Hsp70-negative counterparts release lipid vesicles that contain large amounts of Hsp70 in their lumen and carry Hsp70 on their lipid surface [15]. In line with these in vitro findings, serum Hsp70 levels were found to be elevated in cancer patients compared to healthy individuals [16]. However, depending on the Hsp70 ELISA test system that was used to determine Hsp70 in serum, the detected Hsp70 levels varied from pg/ml [17-19] to several µg/ml [20]. This finding might be due to the fact that most commercially available ELISA kits are optimized and validated for the detection of free Hsp70 in buffer but not in serum. Furthermore, if undiluted serum is used in the ELISA test [21], matrix effects need to be considered that might negatively influence the detection of Hsp70.

Presently, two major pathways are discussed as possible mechanisms for the secretion of Hsp70 by tumor cells. On the one hand, Hsp70 can be released by dying cells as a free protein, on the other hand, evidence is accumulating that a major proportion of extracellular Hsp70 is actively released by living tumor cells with an intact plasma membrane via vesicular export [15]. Protein profiling of tumor-derived lipid vesicles revealed the presence of cytosolic and endosomal proteins including Hsp70 and Rab-4 and the absence of Endoplasmic Reticulum (ER)-derived proteins. In accordance with these findings, ER/Golgi perturbing drugs like monensin and brefeldin A did not negatively impact the release of Hsp70-containing vesicles from tumor cells [22]. The floating properties on a sucrose gradient, the small size and the high acetylcholinesterase activity of these tumor-derived vesicles characterized them as exosomes [15]. The formation of exosomes involves Multivesicular Bodies (MVBs), which are formed by an inward budding of the endosomal membrane [23]. After fusion of the MVBs with the plasma membrane, exosomes with a size of 50-100 nm are secreted into the extracellular space [24]. Apart from tumor cells, a variety of cell types have been described to release exosomes, including different hematopoietic cells, intestinal epithelial cells, Schwann cells, neuronal cells, adipocytes and fibroblasts [25, 26] and therefore, exosomes can be found in several different biological fluids like serum, plasma, urine, breast milk, ascites, synovial fluid and broncho-alveolar lavage fluid [25]. Since exosomes are produced by a double inversion of the plasma membrane, protein content and orientation of proteins in the exosomal membrane reflect that of the plasma cell membrane from which they are derived [27]. As a result, tumor cells that express Hsp70 on their plasma membrane secrete exosomes that also exhibit Hsp70 on their surface [15]. Similarly, the protein composition in the exosomal lumen reflects that of the cytosol of the respective cell. Therefore, it is assumed that exosomes derived from normal cells carry low amounts of Hsp70, whereas exosomes from tumor cells with a high cytosolic Hsp70 content contain high amounts of Hsp70 in their lumen and present it on their lipid surface [23].

However, although, it has been observed that Hsp70 is a promising biomarker for tumor detection future studies in larger cohorts and longer follow-up periods were demanded to determine the role of Hsp70 levels as a universal tumor biomarker. (Gehrmann et al., Radiat Oncol. 9 (2014) 131), most probably due to the fact that currently available ELISA assays have been considered too inefficient to be used as a sensitive and/or quantitative assay [17-20].

The above technical problems are solved by the embodiments characterized in the claims and described further below and illustrated in the Examples and Figures.

SUMMARY OF THE INVENTION

The present invention provides a novel kit and assay for free and lipid-bound (exosomal) heat shock protein 70 (Hsp70), hereinafter also referred to as "lipHsp70 assay" in order to indicate the possibility of the kit and assay, respectively, to efficiently detected the presence of Hsp70 bound in exosomes which are released von viable Hsp70 expressing tumor cells and which Hsp70 species represents the main form of circulating Hsp70 in the body fluid of tumor patients. More specifically, a novel lipHsp70 sandwich ELISA which specifically detects the inducible form of Hsp70 and does not cross-react with the highly homologous constitutive form Hsc70 is provided.

Accordingly, in one aspect the present invention relates to an in vitro method for assaying free and lipid-bound (exosomal) heat shock protein 70 (Hsp70) in a sample derived from a body fluid of a subject, characterized in that the level of Hsp70 is determined by an anti-Hsp70 antibody (mAb) which is antibody cmHsp70.1 as produced by hybridoma cmHsp70.1 (Accession Number DSM ACC2629), or cmHsp70.2 as produced by hybridoma cmHsp70.2 (Accession Number DSM ACC2630), or a HSP70-binding fragment or biotechnological or synthetic derivative thereof.

As illustrated in the appended Examples and further confirmed by Breuninger et al., J. Clin. Cell Immunol. 5 (2014), 264; Gunther et al., Front. Immunol. 6 (2015), 556, experiments performed in accordance with the present invention were successful in the development of an in vitro method, in particular a novel lipHsp70 ELISA which specifically detects the inducible form of Hsp70 and does not cross-react with the highly homologous constitutive form Hsp70. The detection reagent in the lipHsp70 ELISA is the cmHsp70.1 monoclonal antibody, which is directed against an epitope that is exposed on the cell surface of tumor cells and tumor-derived exosomes [28, 29]. Lipid-bound Hsp70 that exerts a different conformation can only be detected by cmHsp70.1 mAb but not by other Hsp70-specific antibodies, see Example 5 as well as FIGS. 1 and 6. Thus, the cmHsp70.1 monoclonal antibody detects approx. 85% lipid-bound Hsp70 whereas the recovery rate of commercially available ELISA assays is less than 10%, see FIG. 6B.

In a previous study, Gehrmann et al., Radiat Oncol. 9 (2014) 131 membrane-bound and soluble Hsp70 as a potential biomarker for tumor detection in 21 patients with squamous cell carcinoma (SCCHN). However, membrane-bound Hsp70 was determined on single cell suspensions of tumor biopsies and reference tissues using mouse monoclonal antibody specific for membrane-bound Hsp70 (cmHsp70.1 by flow cytometry, while serum of the SCCHN patients and healthy donors were only analyzed for soluble free Hsp70 by a commercial available ELISA kit with an antibody that does not (specifically) recognize membrane-bound Hsp70. General drawbacks of this study are that the soluble Hsp70 in the serum might be composed of two different sources, i.e. free and lipid-bound Hsp70, the latter which could only be identified by flow cytometry but not by ELISA. Furthermore, only a relatively small cohort of tumor patients was tested. In addition, general concerns with respect to the difficulty to obtain tumor biopsies and reference material, their mechanical disintegration and cell isolation through a sterile mesh which potentially will result in the loss of tumor cells that express Hsp70 on the membraneas well as the recovery rate of commercially available ELISA kit to detect lipid-bound Hsp70 as discussed, supra, remain.

The term "Hsp70" as used herein refers to the 70 kDa heat shock protein, encoded by three very closely related paralogs (HSPA1A, HSPA1B, and HSPA1L) being a stress-induced protein, as described in [1, 2].

Preferred samples in which to assay exosomal Hsp70 and total Hsp70, respectively, are samples body fluids from an animal, typically from a mammal, preferably from a human, which can include, among other body fluids: blood, serum, plasma, urine, saliva, semen, breast exudate, cerebrospinal fluid, tears, sputum, mucous, lymph, cytosols, ascites, pleural effusions, amniotic fluid, bladder washes and bronchioalveolar lavages. Preferred body fluids to assay are derived from blood, preferably serum or plasma. Particularly preferred body fluid samples include pretreatment samples and samples taken from a patient who has not responded to treatment.

Antibody cmHsp70.1 is a mouse monoclonal anti-Hsp70 antibody (mAb), originally disclosed in international application WO 2005/054295 and Multhoff, Methods 43 (2007), 229-237 and was raised against a peptide immunogen comprising residues 450-463 within the C-terminal substrate binding domain of human Hsp70 (SWISS-PROT entry no. P08107). The cmHsp70.1 antibody recognizes a non-conserved 8-mer epitope within the C-terminal oligomerization domain of the stress-inducible Hsp70, which is not recognized by other Hsp70 antibodies [11, 12]. This antibody was shown to be effective for the sensitive detection of membrane-bound Hsp70 both on human and murine cancer cell lines using biochemical methods, flow cytometry and in vivo imaging; see, e.g., international application WO 2005/054295 and Stangl et al., J. Immunol. 176 (2006), 6270-6276. However, while the cmHsp70.1 antibody has been suggested for targeting and detecting viable tumor cells in the human body, experiments performed in the accordance with the present invention surprisingly revealed the property of that antibody to detect liposomal Hsp70 forms, i.e. Hsp70 in exosome-like lipid vesicles actively released form Hsp70 membrane-positive tumor cells in serum and plasma in a qualitative and qualitative manner with a detection/recovery rate of about 75% and sensitivity in sandwich ELISA in the order of a magnitude higher compared commercially available ELISA kits for the detection of fee and exosomal Hsp70; see also the Examples.

Hsp70-binding fragments of the cmHsp70.1 antibody as well as biotechnological and synthetic derivatives thereof are described in international application WO 2005/054295 and Friedrich et al., Protein Engineering, Design & Selection 23 (2010), 161-168 and include, for example, a single chain Fv fragment, F(ab') fragment, an F(ab) fragment, and an F(ab')2 fragment as well as chimeric derivatives of the cmHsp70.1 antibody.

Preferably, biotechnological and synthetic derivative of the cmHsp70.1 antibody comprises at least one complementary determining region (CDR) as determined according to Kabat of monoclonal antibody cmHsp70.1 or cmHsp70.2. The amino acid sequence of the variable region and of antibody cmHsp70.1 and CDRs are described by Friedrich et al. (2010), supra, in FIG. 1 and Zettlitz et al., Mol. Biotechnol. 46 (2010), 265-278, in FIG. 1. Furthermore, Friedrich et al., (2010) describes the cloning of the Fab fragment of cmHsp70.1 and chimeric versions thereof using different expression constructs, wherein the Fab fragment showed high and specific Hsp70 binding activity in ELISA and SPR measurements as well as sensitive recognition of the membrane-associated Hsp70 on tumor cell lines both in immunofluorescence microscopy and flow cytometry. Thus, Hsp70-binding fragments of the cmHsp70.1 antibody as well as biotechnological and synthetic derivatives thereof suitable in the lipHsp70 assay of the present invention exhibit the immunological binding characteristics of monoclonal antibody cmHsp70.1 and are characterized by being capable of binding membrane-associated Hsp70 on tumor cell lines as determined in international application WO 2005/054295 and Friedrich et al., (2010), preferably binding Hsp70 at an epitope comprising or consisting of residues 450-463 of Hsp70; see, supra. Preferably, the biotechnological and synthetic derivative of the cmHsp70 antibody, respectively, comprises in its variable heavy and/or light chain at least one, two or all three CDRs of the variable heavy and light chain of the original cmHsp70.1 antibody.

Preferably, the biotechnological and synthetic derivative of the cmHsp70.1 antibody exhibits substantially the same rate of recovery of spiked, i.e. lipid-associated Hsp70 in buffer and serum samples as shown in the appended Examples for the subject cmHsp70.1 antibody. Preferably, the average recovery rate for spiked Hsp70 as determined in accordance with the method described in the Examples is at least 60%, more preferably at least 70% and most preferably at least about 75%, i.e. 78±3%. In one embodiment of the present invention, the anti-Hsp70 antibody is capable of binding free and lipid-bound (exosomal) Hsp70 with substantially the same level of affinity, specificity and/or recovery rate like exemplary antibody cmHsp70.1±10%; see Example 2-4 and FIGS. 3-5.

Suitable body fluid samples can be blood, serum, plasma, urine, saliva, semen, breast exudate, cerebrospinal fluid, tears, sputum, mucous, lymph, cytosols, ascites, pleural effusions, amniotic fluid, bladder washes and bronchioalveolar lavages, cerebrospinal fluid (CSF) among other body fluid samples. Preferred body fluids, for example, include serum, or plasma samples treated with heparin, citrate or EDTA, among other body fluid samples, and can be fresh or frozen. As known in the art, plasma is the liquid component of blood which holds the blood cells in suspension further containing dissolved proteins, e.g. serum albumins, globulins, glucose, clotting factors, electrolytes, hormones, and carbon dioxide. Serum is plasma without blood cells or clotting factors. Serum includes all proteins not used in blood clotting (coagulation) and electrolytes, antibodies, antigens, hormones, and any exogenous substances, e.g., drugs and microorganisms. Thus, the sample used in the method is substantially free of cells, in particular free of viable tumor cells. As illustrated in Examples 2 to 4 and shown in FIGS. 2 to 5 the lipHsp70 ELISA is equally suitable for serum and plasma and the measured Hsp70 concentrations were not impacted by food intake, repeated freezing and thawing of the sample or moderate hemolysis. Thus in a preferred embodiment of the method of the present invention the body fluid is blood and the sample comprises serum or plasma, or urine; preferably wherein the serum is separated from blood by centrifugation after allowing to clot.

The subject to be diagnosed may be asymptomatic or preclinical for the disease. Preferably, the control subject has a disease associated with increased levels of Hsp70, wherein a similarity between the level of Hsp70 and the reference standard indicates that the subject to be diagnosed has a disease or is at risk to develop disease related to increased levels of free and lipid-bound (exosomal) Hsp70. Alternatively, or in addition as a second control the control subject does not show increased levels of Hsp70, wherein a difference between the level of physiological Hsp70 and the reference standard indicates that the subject to be diagnosed has a disease or is at risk to develop disease related to increased levels of free and lipid-bound (exosomal) Hsp70. Preferably, the subject to be diagnosed and the control subject(s) are age-matched As summarized in Table 2 as wells as shown in Example 6 and FIG. 7 a total of 114 age- and gender-matched samples from tumor patients and healthy donors were quantified using the herein described lipHsp70 ELISA. Significantly higher Hsp70 levels were found in all tumor patient cohorts compared to the healthy controls. Furthermore, as described in Example 6 a Receiver Operating Characteristic (ROC) curve analysis was performed by comparing serum Hsp70 levels of healthy donors with those of the different patient cohorts (FIG. 6B). This analysis revealed an "Area Under the Curve" (AUC; CI 95%) and sensitivity for a cut-off value of 7.7 ng/ml (derived from the 75th percentile of the healthy donors) (Table 2). Remarkably, the specificity was 75% for all patient groups. Therefore, preferably the amount of free and lipid-bound (exosomal) Hsp70 in samples from a healthy human subject ranges from 1500 to 2000 pg/ml, preferably from 2000 to 4000 pg/ml, more preferably from 4000 to 6000 pg/ml. In contrast, the amount of free and lipid-bound (exosomal) Hsp70 in samples from a tumor patient, ranges from 10 to 15 pg/ml, preferably from 15 to 30 pg/ml, more preferably from 30 to 60 pg/ml.

In addition, a total of 100 age- and gender-matched samples from patients with relapsing remitting multiple sclerosis (RRMS), non-relapsing remitting multiple sclerosis (non-RRMS), other inflammatory neurological diseases (OIND) and non-inflammatory neurological diseases (NIND) were quantified for Hsp70 levels using the lipHsp70 ELISA of the present invention; see Table 4A to 4C as well as Example 7 and FIG. 8. As shown in FIG. 8A significantly higher Hsp70 levels were found in all patients with multiple sclerosis (MS), followed by Hsp70 levels in patients with other inflammatory neurological diseases (OIND) compared to patients with non-inflammatory neurological diseases (NIND) and the healthy controls. Furthermore, it was found that Hsp70 is supportive in distinguishing relapsing remitting multiple sclerosis (RRMS) and non-relapsing remitting multiple sclerosis (non-RRMS) (FIG. 8B). Remarkably, the specificity of detecting Hsp70 was 67% over the threshold for patients with multiple sclerosis (MS) (FIG. 8C). Therefore, preferably the amount of free and lipid-bound (exosomal) Hsp70 in samples from a patient with a non-inflammatory neurological diseases (NIND) ranges from 2200 to 13000 pg/ml, preferably from 6000 to 9000 pg/ml, more preferably from 7000 to 8000 pg/ml. In contrast, the amount of free and lipid-bound (exosomal) Hsp70 in samples from a patient with another inflammatory neurological diseases (OIND) ranges from 5800 to 30000 pg/ml, preferably from 11000 to 18000 pg/ml, more preferably from 12000 to 16000 pg/ml. Further, the amount of free and lipid-bound (exosomal) Hsp70 in samples from a patent with non-relapsing remitting multiple sclerosis (non-RRMS) ranges from 3500 to 19000 pg/ml, preferably from 7000 to 13000 pg/ml, more preferably from 8000 to 11000 pg/ml. In addition, the amount of free and lipid-bound (exosomal) Hsp70 in samples from a patent with relapsing remitting multiple sclerosis (RRMS) ranges from 1500 to 6000 pg/ml, preferably from 2500 to 4500 pg/ml, more preferably from 3000 to 4000 pg/ml.

Thus, in a preferred embodiment of the method of the present invention an elevated level of Hsp70 compared to a control sample derived from a healthy subject is indicative for a tumor or an inflammatory disease, preferably multiple sclerosis (MS).

In a preferred embodiment, the present invention relates to the detection and monitoring of outcome of radiation therapy, chemotherapy or surgery in patients with tumors, since viable tumor but not normal cells frequently overexpress lipid-bound (exosomal) Hsp70 and present it on their cell surface from where it can be actively released. In an even more preferred embodiment, Hsp70 could be used as is a predictor of inflammatory diseases, e.g. to monitor the future risk of death and myocardial infarction in patients with suspected or known adverse cardiovascular outcomes (Eapen et al., J Am Coll Cardiol. 62 (2013) 329-37) or to monitor Hsp70 levels in peripheral and renal vascular disease (Wright et al., Heart Vessels 15 (2000) 18-22) to monitor Hsp70 levels in patients with multiple sclerosis (MS) and other inflammatory neurological disease (OIND) such as chronic inflammatory demyelinating polyneuropathy (CIDP), traumatic brain injury, acute disseminated encephalomyelitis (ADEM), optic neuritis (ON), transverse myelitis or neuromyelitis optica (NMO), Alzheimers's disease, Parkinson's disease, sepsis in the brain. In an alternative embodiment, the method of the present invention can be used to monitor the treatment of a tumor in subject with an anti-tumor agent or determining the therapeutic utility of a candidate anti-tumor agent, e.g. it has been shown previously that elevated Hsp70 levels can act as a read-out for the efficacy of Hsp90 inhibitor-based therapies (Dakappagari et al., Biomarkers 15 (2010) 31-38). In a further embodiment, the method of the present invention can be used to monitor the treatment of a multiple sclerosis (MS) patient for example with interferon or other agents which are sought to ameliorate the symptoms of MS or determining the therapeutic utility of a candidate agent for the treatment of multiple sclerosis.

In this context, by "subject" or "individual" or "animal" or "patient" or "mammal" is meant any subject, particularly a mammalian subject, e.g., a human patient, for whom diagnosis, prognosis, prevention, or therapy is desired. However, the lipHsp70 assay of the present invention is also contemplated for use at various stages in drug discovery including for example animal trials for investigating the therapeutic effectivity of an anti-tumor agent anti-multiple sclerosis (MS) agent.

As mentioned above, the inventors of the present invention were successful in demonstrating an increased level of Hsp70 in tumor patients compared to healthy controls (Table 2) as well as multiple sclerosis (MS) patients compared to other inflammatory neurological diseases (OIND), non-inflammatory neurological diseases (NIND) and healthy controls showing highest values for patients with MS and OIND followed by lower values in non-RRMS and lowest values in patients with RRMS. Therefore, the method of the present invention is in principle feasible to, but not limited to therapeutically monitor radiotherapy, chemotherapy or surgical treatment of cancer patients. Furthermore, chronic inflammatory disorders such as multiple sclerosis (MS) in which cell death occurs can be detected by assaying the amount of free Hsp70 released from apoptotic cells. In summary, the method provided by the present invention is advantageous in monitoring the vital mass of tumors, since only living tumors secrete lipid-bound (exosomal) Hsp70, however, free Hsp70 released from apoptotic cells can be detected in addition. Accordingly, due to the fact that the level and liposomal (exosomal) Hsp70 circulating in the body fluid correlates with the viable tumor cell load and thus metastasis one hand or the presence of multiple sclerosis (MS) and the high recovery rate of the lipHsp70 assay for exosomal Hsp70 the assay of the present invention can be used to diagnose or prognose a disease, in particular a tumor or an inflammatory disease, preferably multiple sclerosis (MS).

Hence, the method of the present invention is preferably used for (i) diagnosing a tumor in a subject or whether a cancer patient is amenable to the treatment with an anti-tumor agent, in particular Hsp70 specific agent, respectively, wherein an elevated level of Hsp70 compared to a control sample is indicative for the tumor and possibility for the treatment with the agent, respectively; or (ii) monitoring the treatment of a tumor in subject with an anti-tumor agent or determining the therapeutic utility of a candidate anti-tumor agent, comprising determining the level of Hsp70 in the sample obtained from the subject following administration of the agent to the subject, wherein a reduced level of Hsp70 in the sample of the subject compared to a control indicates progress in the treatment and therapeutic utility of the agent, respectively, or (i) diagnosing multiple sclerosis (MS) in a subject or whether a MS patient is amenable to the treatment with an anti-multiple sclerosis agent, in particular Hsp70 specific agent, respectively, wherein an elevated level of Hsp70 compared to a control sample is indicative for multiple sclerosis (MS) and possibility for the treatment with the agent, respectively; or (ii) monitoring the treatment of multiple sclerosis (MS) in subject with an anti-multiple sclerosis agent or determining the therapeutic utility of a candidate antineoplastic agent, comprising determining the level of Hsp70 in the sample obtained from the subject following administration of the agent to the subject, wherein a reduced level of Hsp70 in the sample of the subject compared to a control indicates progress in the treatment and therapeutic utility of the agent, respectively.

The term "diagnostic/prognostic" is herein defined to encompass the following processes either individually or cumulatively depending upon the clinical context: determining the presence of disease, determining the nature of a disease, distinguishing one disease from another, forecasting as to the probable outcome of a disease state, determining the prospect as to recovery from a disease as indicated by the nature and symptoms of a case, monitoring the disease status of a patient, monitoring a patient for recurrence of disease, and/or determining the preferred therapeutic regimen for a patient. The diagnostic/prognostic methods of this invention are useful, for example, for screening populations for the presence of a tumor, determining the risk of developing a tumor, diagnosing the presence of a tumor, monitoring the disease status of patients with a tumor, determining the prognosis for the course of a tumor, evaluating the efficacy of an anti-tumor drug and treatment, respectively, as well as drug screening in laboratory non-human animals typically use in drug development such as mice, rats, gerbils, cats, dogs, horses and cows.

Furthermore, the diagnostic/prognostic methods of this invention are useful, for example, for screening populations for the presence of multiple sclerosis (MS), determining the risk of developing multiple sclerosis (MS), diagnosing the presence of multiple sclerosis (MS), monitoring the disease status of patients with multiple sclerosis (MS), determining the prognosis for the course of multiple sclerosis (MS), evaluating the efficacy of an anti-multiple sclerosis (MS) drug and treatment, respectively, as well as drug screening in laboratory non-human animals typically use in drug development such as mice, rats, gerbils, cats, dogs, horses and cows.

The present invention is useful for screening for the presence of a wide variety of inflammatory disorders, cardiovascular diseases and in particular tumors as indicated above. Such an assay can be used to detect tumors, monitor their growth, and help in the diagnosis and prognosis of a tumor. The assays can also be used to detect the presence of cancer metastasis, as well as confirm the absence of tumor tissue following cancer chemotherapy and/or radiation therapy. It can further be used to monitor cancer chemotherapy and tumor reappearance. Furthermore, such an assay can be used to detect multiple sclerosis (MS) and help in the diagnosis and prognosis of multiple sclerosis (MS). The assays can also be used to detect the presence of multiple sclerosis (MS), as well as confirm the absence of symptoms of multiple sclerosis (MS) following multiple sclerosis (MS) therapy. It can further be used to distinguish relapsing remitting multiple sclerosis (RRMS) and non-relapsing remitting multiple sclerosis (non-RRMS); see, e.g., Example 7 and FIG. 8B.

In a preferred embodiment of the invention, total Hsp70 is quantitated in human body fluid samples drawn serially over time. Such body fluid specimens can be taken pretreatment, during treatment, or post-treatment, or can be taken from a patient who is not responding to therapy. As used herein, "serial changes over time" or "serial samples" denotes sequential testing of samples taken over time periods which would be considered relevant for the subject, depending on the context and the circumstances. For example, for cancer patient screening, serial samples might be drawn upon a patient's initial visit, after diagnosis, pre-surgery and/or post-surgery; whereas for population screening for a tumor, serial samples might be drawn on a yearly basis. Similarly, for drug screening serial samples may be taken from a laboratory animal, for example prior and various times after drug treatment. Furthermore, for multiple sclerosis (MS) patient screening, serial samples might be drawn upon a patient's initial visit, after diagnosis, and during multiple sclerosis (MS) treatment; whereas for population screening for multiple sclerosis (MS), serial samples might be drawn on a yearly basis. Similarly, for drug screening serial samples may be taken from a laboratory animal, for example prior and various times after drug treatment.

The implication of elevated levels of circulating Hsp70 has also been observed in inflammatory and cardiovascular diseases such as chronic heart failure, after acute myocardial infarction (AMI), dilated cardiomyopathy, and electrocardiography abnormality thereby suggesting that Hsp70 might possibly play a harmful role in the pathogenesis and progression of atherosclerosis or cardiovascular diseases; see, e.g., Zhang et al., Cell Stress and Chaperones 15 (2010), 675-686, wherein ELISA has been used in order to determine a correlation of higher Hsp70 levels with a higher risk of acute coronary syndrome (ACS) and references cited therein. However, also here the ELISA kit employed (Stressgen Biotechnologies Corp, EKS-715 and EKS-750) only detected a level about 1 to 5 ng/ml.

As known in the art, various possibilities exist to detect Hsp70 using an anti-Hsp70 antibody including, but not limited to direct assays such as antibody arrays, antibody-loaded beads, nanoparticles or any other vehicle being suitable to immobilize an antibody. The methodology of antibody arrays is well-known in the art; see, e.g. Chang, J. Immunol. Methods 65 (1983), 217-223, international applications WO 1984/003151 and WO1988/008538 as well as U.S. Pat. No. 4,829,010. Furthermore, methods for coupling antibodies, e.g. to beads or nanoparticles are well-known in the art, in particular commercially available kits such as the Dynabeads® Antibody Coupling Kit or Thermo Scientific Pierce® Protein G Magnetic Beads allow easy coupling of an antibody of your choice to the surface of uniform beads. In addition, an antibody-based array may be used, which is for example loaded with antibodies or equivalent antigen-binding molecules of the present invention which specifically recognize Hsp70. Design of microarray immunoassays is summarized in Kusnezow et al., Mol. Cell Proteomics 5 (2006), 1681-1696. Accordingly, the present invention also relates to microarrays loaded with Hsp70-binding molecules identified in accordance with the present invention.

Typically, in the method of the present invention the anti-Hsp70 antibody comprises a detectable label, preferably wherein the detectable label is selected from the group consisting of an enzyme, a radioisotope, a fluorophore, a heavy metal, a tag or a ligand such as fluorescent labels, enzyme labels, free radical labels, avidin-biotin labels, or bacteriophage labels. One of the ways in which an antibody, or antigen-binding fragment, variant, or derivative thereof can be detectably labeled is by linking the same to an enzyme and using the linked product in an enzyme immunoassay (EIA) (Voller, A., "The Enzyme Linked Immunosorbent Assay (ELISA)" Microbiological Associates Quarterly Publication, Walkersville, Md., Diagnostic Horizons 2 (1978), 1-7); Voller et al., J. Clin. Pathol. 31 (1978), 507-520; Butler, Meth. Enzymol. 73 (1981), 482-523; Maggio, (ed.), Enzyme Immunoassay, CRC Press, Boca Raton, Fla., (1980); Ishikawa, et al., (eds.), Enzyme Immunoassay, Kgaku Shoin, Tokyo (1981). The enzyme, which is bound to the antibody, will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. Additionally, the detection can be accomplished by colorimetric methods which employ a chromogenic substrate for the enzyme. Detection may also be accomplished by visual comparison of the extent of enzymatic reaction of a substrate in comparison with similarly prepared standards.

In one embodiment of the method of the present invention the substrate is a chromophore selected from the group of 3,3'-diaminobenzidine (DAB), 3-amino-9-ethylcarbazole (AEC), 4-chloro-1-naphtol (CN), 3,3'-5,5'-tetramethylbenzidine (TMB), New Fuchsin, naphthol-AS-MX-phosphate, 5-bromo-5-chloro-3-indoxyl phosphate (BCIP), Nitro blue tetrazolium chloride (NBT), 5-bromo-4-chloro-3-indoxyl-β-D-galactopyranoside (X-Gal), 5-bromo-3-indolyl-β-D-galactopyranoside (Blue-Gal), 6-chloro-3-indolyl-β-D-galactopyranoside (Y-Gal), 5-iodo-3-indolyl-β-D-galactopyranoside (Purple-Gal), 5-bromo-6-chloro-3-indolyl-β-D-galactopyranoside (Magenta-Gal), N-methylindolyl-β-D-galactopyranoside (Green-gal), 4-methylumbelliferyl-β-D-galactopyranoside (MUG), which upon reaction with a ligand-binding tag, preferably an enzyme shows a color reaction.

Typically, the level of Hsp70 in the method of the present invention is determined by subjecting the sample to an anti-Hsp70 antibody and detecting the presence of the complex formed between Hsp70 and the antibody. Detection may also be accomplished using any of a variety of other immunoassays. For example, by radioactively labeling the antibody, or antigen-binding fragment, variant, or derivative thereof, it is possible to detect the antibody through the use of a radioimmunoassay (RIA) (see, for example, Weintraub, B., Principles of Radioimmunoassays, Seventh Training Course on Radioligand Assay Techniques, The Endocrine Society, (March, 1986)), which is incorporated by reference herein). The radioactive isotope can be detected by means including, but not limited to, a gamma counter, a scintillation counter, or autoradiography. In a preferred embodiment of the method of the present invention the level of Hsp70 is determined by Enzyme-linked immunosorbent assay (ELISA), preferably sandwich ELISA. An exemplary and preferred immunoassay according to the methods of the invention is a sandwich ELISA described below in the Materials and Methods section, and was used to obtain the data for Examples 1 to 6. It can be appreciated that alternate methods, in addition to those disclosed herein, can be used to quantify free and lipid-bound (exosomal) Hsp70 in body fluids. Other preferred sandwich assays could be used with other visualizing means, such as luminescent labels. Other labels are detailed above and are otherwise known in th art. Many formats can be adapted for use with the methods of the present invention. The detection and quantitation of free and lipid-bound (exosomal) Hsp70 in human body fluids can be performed, for example, by enzyme-linked immunosorbent assays, radioimmunoassays, dual antibody sandwich assays, agglutination assays, fluorescent immunoassays, immuno-electron and scanning microscopy using immunogold, among other assays commonly known in the art. The quantitation of free and lipid-bound (exosomal) Hsp70 in such assays can be adapted by conventional methods known in the art. In preferred embodiments, serial changes in circulating free and lipid-bound (exosomal) Hsp70 levels, or such levels in other body fluids, are detected and quantified by a sandwich assay in which the capture antibody has been immobilized, using conventional techniques, on the surface of the support.

Suitable supports used in assays include among other supports, synthetic polymer supports, such as polypropylene, polystyrene, substituted polystyrene, polyacrylamides (such as polyamides and polyvinylchloride), glass beads, agarose, and nitrocellulose, among other supports.

An exemplary and preferred ELISA sandwich immunoassay is described in the Materials and Methods section and in Examples 1 to 7. That exemplary ELISA uses a rabbit polyclonal antibody directed against human recombinant Hsp70 (Davids, Biotechnologie, Regensburg, Germany) as the capture antibody and biotinylated cmHsp70.1 (multimmune, Munich, Germany) as the detector antibody. The capture antibody is immobilized on microtiter plate wells; diluted human serum/plasma samples or Hsp70 standards (recombinant Hsp70) are incubated for 2 hours at 27° C. in the wells to allow binding of free and lipid-bound (exosomal) Hsp70 by the capture antibody. After washing of wells, the immobilized Hsp70 antigen is exposed to the biotinylated detector antibody 2 hours at 27° C., after which the wells are again washed. A streptavidin horseradish peroxidase conjugate is then added for 1 hour at 27° C. After a final wash, TMB Blue Substrate is added to the wells (and incubated for 30 minutes at 27° C.) to detect bound peroxidase activity. The reaction is stopped by the addition of 2N sulfuric acid, and the absorbance is measured at 450 nm. Correlating the absorbance values of samples with the Hsp70 standards allows the determination of a quantitative value of total Hsp70 in ng/ml of serum or plasma.

Hence, as illustrated in the Examples, in particular Example 3 and FIG. 4 the anti-Hsp70 antibodies used in accordance with the present invention is superior in detecting free and exosomal Hsp70 in a body fluid compared to assays and ELISA kits available so far. Therefore, the present invention generally relates to the use of the cmHsp70.1 antibody, fragment, biotechnological and synthetic derivative thereof as described above for assaying free and exosomal Hsp70 in a test sample, preferably the sample is derived from the body fluid of a subject, preferably wherein the sample comprises serum or plasma.

In addition, thanks to the novel lipHsp70 assay of the present invention described hereinabove and in the Examples the present invention provides and relate to an assay kit adapted to carry out a method the present invention described hereinabove for determining the presence, progression and/or relapse of a tumor in a subject, comprising means for assaying a serum or plasma sample from the subject for free and liposomal Hsp70 and means for comparing the measured level of Hsp70 to a set of reference standard and/or a control.

As further described in the Examples, the present invention for the first time provides an in vitro method, in particular an ELISA, which is a highly sensitive and robust method for measuring liposomal and free Hsp70 in serum and plasma. A comparison of the levels of liposomal Hsp70 using the herein disclosed lipHsp70 ELISA and the control ELISA revealed large differences (FIG. 6A). The recovery of liposomal Hsp70 using the lipHsp70 ELISA was 76±5%, whereas that of the control ELISA was only 7±1%. These data indicate that the detection of lipid-associated Hsp70 was more than 10-fold better with the lipHsp70 ELISA than with the control ELISA (FIG. 6B). Accordingly, an Hsp70 eight point standard is included into each assay test preferably using 0-50 ng/ml recombinant Hsp70 diluted in Cross-Down Buffer.

Thus, in a further aspect, the present invention relates to a kit for the lipHsp70 assay of the present invention, i.e. lipHsp70 ELISA kit for determining the presence of free and exosomal Hsp70 in a test sample comprising:
(i) a detection reagent comprising antibody cmHsp70.1 or cmHsp70.2 or a Hsp70-binding fragment or biotechnological or synthetic derivative thereof as described hereinbefore, optionally conjugated to a detectable label or ligand;
(ii) a capture reagent for Hsp70 which is different from the detection reagent of (i);
(iii) optionally a detectable label conjugated to a ligand-binding tag; preferably
(iv) a calibrated immunoassay standard or control of recombinant human Hsp70; and optionally (v) recommendations for microplates, buffers, diluents, substrates and/or solutions as well as instructions how to perform the lipHsp70 assay described herein.

Suitable capture reagents for Hsp70, in particular polyclonal antibodies against recombinant human Hsp70, detectable labels/ligands, ligand-binding tag; calibrated immunoassay standards and controls of recombinant human Hsp70 as well as recommendations for microplates, buffers, diluents, substrates and/or solutions as well as instructions how to perform an Hsp70 ELISA are generally known; see, e.g., commercially available Hsp70 kits from Human/Mouse/Rat Total Hsp70/HspA1A DuoSet IC (R&D Systems, Minneapolis, Minn., USA), containing the basic components required for the development of sandwich ELISAs to measure Hsp70/HspA1A in cell lysates. An immobilized capture antibody specific for Hsp70/HspA1 A binds both phosphorylated and unphosphorylated Hsp70/HspA1A. After washing away unbound material, a biotinylated detection antibody is used to detect both phosphorylated and unphosphorylated protein, utilizing a standard Streptavidin-HRP format. However, compared to the DuoSet IC kit, the detection antibody is the cmHsp70.1 antibody or derivative thereof as described herein. Furthermore, due to the significant higher sensitivity of the lipHsp70 assay of the present invention, the calibrated standard and control, respectively, is adapted thereto and shifted to a corresponding increased high standard and higher serial dilutions of human recombinant Hsp70 compared those in the prior art kit; see also the Examples where an Hsp70 eight point standard was included into each ELISA test using 0-50 ng/ml recombinant Hsp70.

In a particularly preferred embodiment, the present invention relates to the lipHsp70 ELISA kit, wherein
(i) the detection reagent comprises an anti-Hsp70 antibody conjugated to a ligand, preferably biotin;
(ii) the capture reagent comprises a polyclonal antibody directed against human recombinant Hsp70;
(iii) the ligand-binding tag is streptavidin conjugated to an enzyme, preferably horseradish peroxidase (HRP); and/or
(iv) the standard comprises a serial dilution of Hsp70 including at least a high standard of ≥15 ng/ml, preferably ≥25 ng/ml and more preferably ≥50 ng/ml.

The kit of the present invention may further comprise artificial Hsp70-containing lipid vesicles and optionally empty control vesicles, or means therefor for determining the rate of recovery of HSP70 for the anti-HSP70 binding molecule compared to the Hsp70 concentration as determined by Western blotting. Further comprising recombinant Hsp70 protein for spiking in samples and optionally buffer in order to determine the rate recovery of Hsp70 for the anti-Hsp70 binding molecule. The kit of claim for use in an ELISA, wherein the recovery of Hsp70 for the anti-Hsp70 antibody is at least 60%, preferably at least 65% and more preferably at least 70% or more.

In one embodiment, the present invention relates to a ready-to-use format of the lipHsp70 ELISA kit comprising:
(i) a biotinylated detection antibody;
(ii) an antibody-coated ELISA well plate with a capture antibody;
(iii) concentrated HRP-conjugated streptavidin;
(iv) calibrated immunoassay standard recombinant human Hsp70
(v) washing buffer;
(vi) assay/sample diluent buffer(s);
(vii) ELISA colorimetric reagent, preferably 3, 3¢, 5, 5¢-tetramethylbenzidine (TMB) in buffer solution; and
(viii) ELISA stop solution, preferably 0.2 M sulfuric acid.

Corresponding ELISA kit format are well known to the person skilled in the art; see, e.g., the Human HSP70 ELISA Kit RAB0216-1KT for serum, plasma, cell culture supernatant and urine (RAB0216 Sigma-Aldrich Co. LLC), which components individually or in combination may be employed in the lipHsp70 ELISA kit of the present invention. Similarly, the HSP70 high sensitivity ELISA kit ADI-EKS-715 (Enzo Life Sciences, Inc.) for quantification of Hsp70 in serum and plasma samples may be employed for the above-mentioned base components.

The kit generally comprise the components as described above, preferably a first container including the biotinylated detection antibody, a second reagent container containing the concentrated HRP-conjugated streptavidin, buffer, i.e. washing buffer, assay buffer, ELISA colorimetric reagent and stop solution. The antibody-coated ELISA well plate with a capture antibody and reagent containers will generally be included together and packaging of the type conventional for immunoassay kits, e.g., boxes, bags, cylinders, shrink wrap cards, and the like.

Optionally, the kit may further include written instructions setting forth the method steps of the present invention as mentioned, supra.

As illustrated in Example 1 and 7 as well as in shown in FIGS. 2 and 8, respectively, the reliability and robustness of the lipHsp70 ELISA together with its ability to detect higher levels of Hsp70 in the circulation of patients with cancer and multiple sclerosis (MS) makes this method a promising tool for monitoring the presence and size of viable tumor mass and the presence or risk of developing multiple sclerosis (MS), as well as therapeutic outcomes. Therefore, it can be expected that a therapeutic agent for use in the treatment of a patient suffering from a tumor will most often be combined with the method and assay, supra, and described in the Examples that quantifies the amount of free and lipid-bound (exosomal) Hsp70.

Hence, the lipHsp70 assay and kit of the present invention can be used in therapy selection for a human patient with a tumor or another disease associated with membrane-bound Hsp70 expression such as inflammatory disorders, preferably multiple sclerosis (MS) and cardiovascular diseases. Accordingly, in a further aspect the present invention relates to a therapeutic agent for use in the treatment of a patient suffering from a disease associated with the expression of Hsp70, preferably a tumor or an inflammatory disease, preferably multiple sclerosis (MS), characterized in that a serum or plasma sample derived from the patient's blood, compared to a control shows an elevated level of Hsp70, preferably wherein the serum level of Hsp70 is higher than about 7.7 ng/ml, preferably higher than 10 ng/ml. For MS patients the Hsp70 values range between 8.0 ng/ml and 13 ng/ml with lowest values at 4 ng/ml and highest levels at 25 ng/ml, for patients with OIND the Hsp70 values range from 10 ng/ml and 18 ng/ml with highest levels at 30 ng/ml and lowest levels at 6 ng/ml.

Diverse approaches which have evolved for Hsp70-based anticancer therapy, including inhibition of activity, modifying of expression levels and anti-tumor vaccines are known to the person skilled in the art; see, e.g., Juhasz et al., Cancers 6 (2014), 42-66 and references cited therein. For example, immunotherapeutic targeting of membrane Hsp70-expressing tumors using recombinant human Granzyme B is described in Gehrmann et al., PLoS ONE 7 (2012): e41341. doi:10.1371/journal.pone.0041341. Hsp70 inhibitors having broad activity as an anti-cancer agent are also known to the person skilled in the art; see, e.g., Balaburski et al., Mol. Cancer Res. 11 (2013), 219-229. Specific examples of Hsp70-based cancer therapy are vaccine ENKASTIM©, cmHsp70.1 derived monoclonal antibody mi-TUMEX© and recombinant human granzyme B mi-APO© developed and offered by multimmune GmbH, Arnulfstr. 197, 80634 Munich, Germany. Agents for the treatment of inflammatory and cardiovascular diseases are also know to the person skilled in the art. For inflammation Cortisol, Fingolimod, β-Interfereones, Teriflumonid, Dimethyl-fumurate, Glatirameracetat, Aspirine, Ibuprofen, and Diclofenac are used, for cardiac diseases: nitrate, Molisidom, β-receptor blockers, Ca-antogonists, ACE-inhibtors, digitalis, HMG-Co reductsa Inhibitor, Marcumar, and Aspirine are used. Therefore, the assay of the present invention, preferably in the form of an ELISA will identify which patients to treat (i.e. patients with high levels of Hsp70). Therefore, advantageously the anti-Hsp70 antibodies cmHsp70.1 and cmHsp70.2 as well as their biotechnological and synthetic derivatives as well as equivalent Hsp70-binding agents are designed to be used together with the novel lipHsp70 ELISA of the present invention, for example as a clinical package, combining components necessary and sufficient to perform the assay and/or instructions for doing so; see supra.

As mentioned, due to high sensitivity and reliability of the lipHsp70 assay the method and kit of the present invention as well as therapeutic agent can be used in context with any disorder and disease associated with an altered, typically increased level of Hsp70 in a body fluid, in particular exosomal Hsp70 which derived from increased membrane-bound expression of Hsp70. Diseases and disorders in which increased levels of free and lipid-bound (exosomal) Hsp70 occur include but are not limited to tumors selected from the group consisting of head and neck cancer, lung cancer, colorectal carcinoma, pancreatic cancer, glioblastoma and hematological malignancies; inflammatory disorders including diseases involving tissue remodeling and/or chronic inflammation including but not limited to multiple sclerosis (MS), fibrotic disease, wound healing, keloid formation, osteoarthritis, rheumatoid arthritis and related disorders involving cartilage degradation, atherosclerotic disease and Crohn's disease, liver cirrhosis, hepatitis, malaria; infections selected from the group consisting of including but not limited to adenovirus, rabies virus, rotavirus, vesicular stomatitis virus, EBV, cytomegalovirus, herpes virus, Tailors virus, noro virus, papilloma virus, Hanta virus, influenza virus, Hepatitis B, C virus, HIV, smallpox and pox virus, BSE, meningoencephalitis, borreliosis; bacterial infections such as Helicobacter, Lyme Borreliosis, Encephalitis, Toxoplasmosis, Sleeping disease, lung inflammation, bladder infections, sepsis, listeriosis; and cardiovascular disease such as coronary heart disease, cardiomyopathy, hypertensive heart disease, heart failure, Congenital heart disease, stroke, peripheral heart disease, rheumatoid heart disease.

Further embodiments of the present invention will be apparent from the description and Examples that follow.

DETAILED DESCRIPTION OF THE INVENTION

Figure 1:
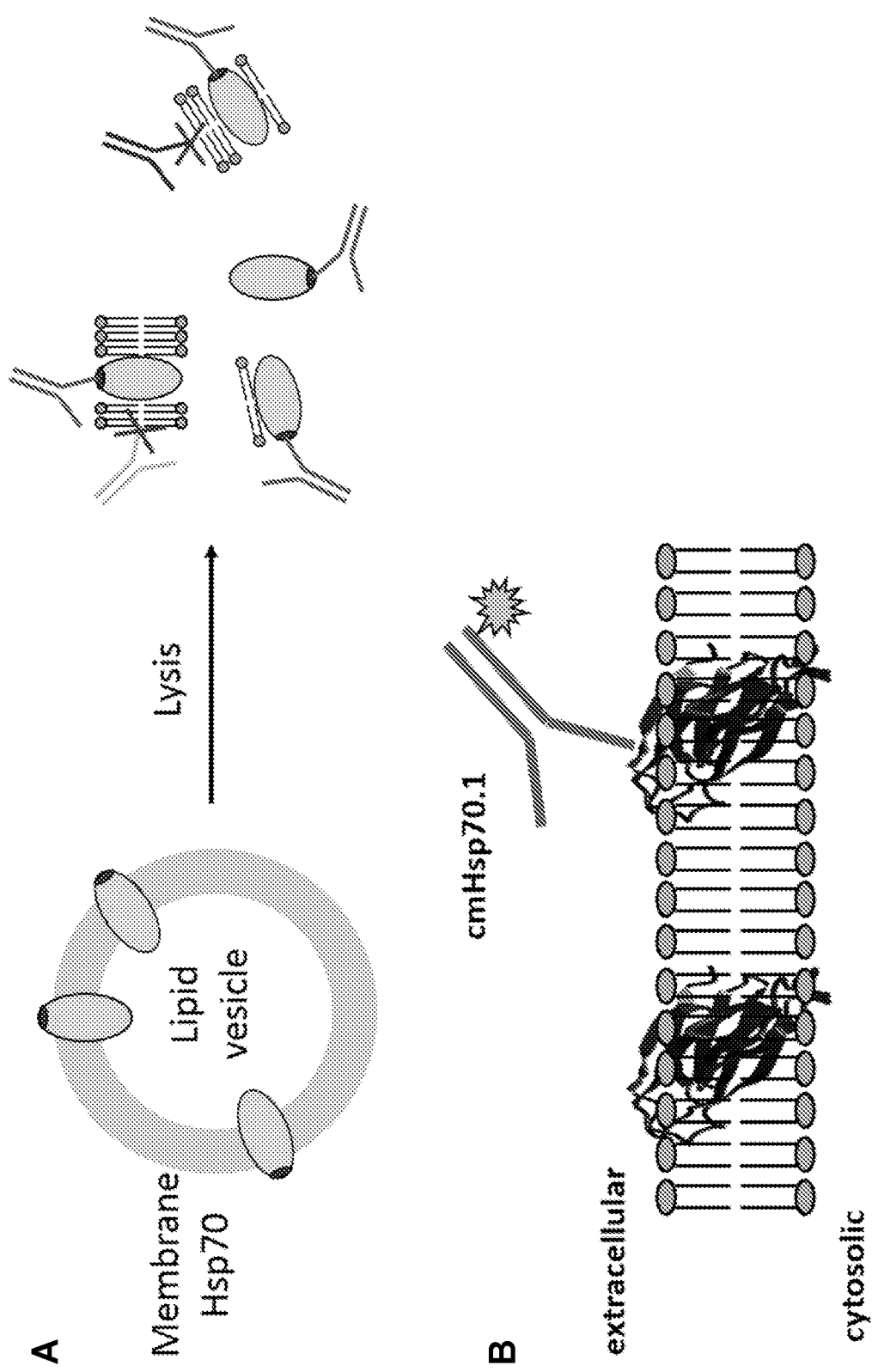
FIG. 1: Lipid-association of Hsp70 in exosomes and in the plasma membrane of living tumor cells. (A) An incomplete solubilisation of lipid vesicles such as exosomes with detergents used in ELISA tests can lead to Hsp70-lipid complexes. Lipid-bound Hsp70 that exerts a different conformation can only be detected by cmHsp70.1 mAb but not by other Hsp70-specific antibodies. (B) The cmHsp70.1 mAb detects Hsp70 on the plasma membrane of living tumor cells. This lipid-bound conformation of Hsp70 in the plasma membrane is similar to that of lipid-bound Hsp70 in exosomes. Therefore, it is speculated that the recovery of lipid-bound Hsp70 with the lipHsp70 ELISA is better than with the control ELISA.
Figure 2:
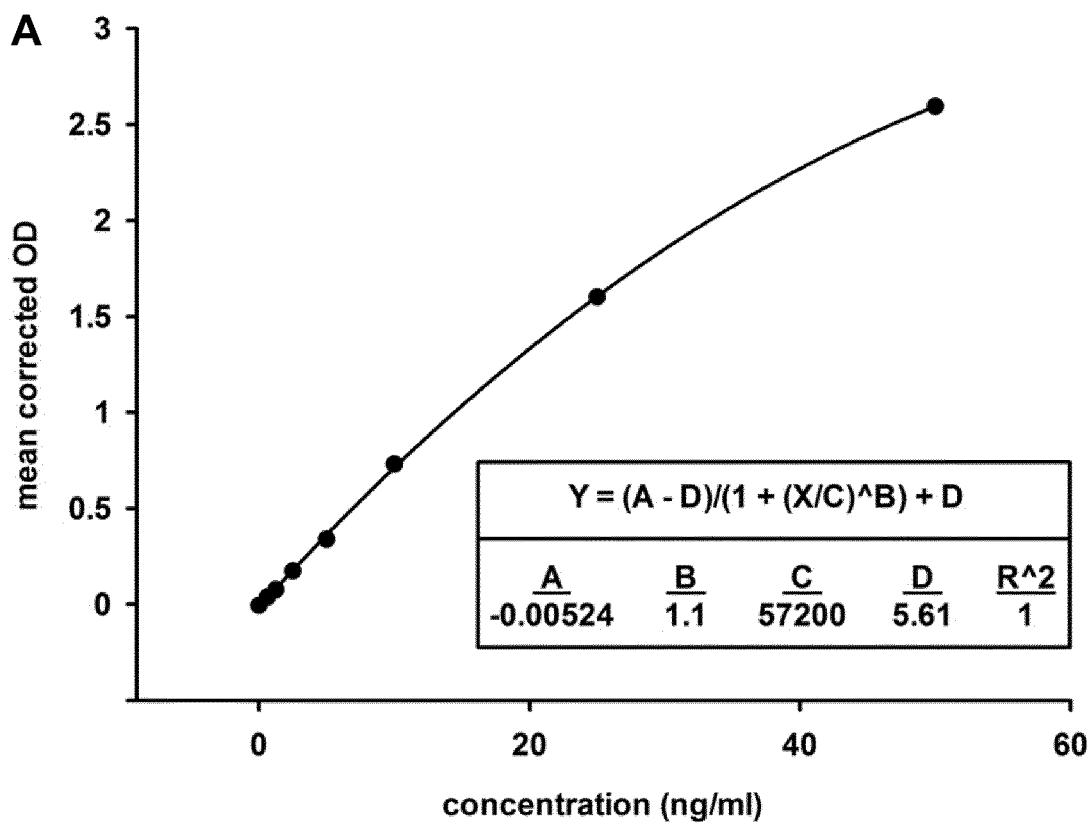
FIG. 2: Validation of the lipHsp70 ELISA. (A) Representative eight point calibration curve obtained from the lipHsp70 ELISA using a four-parameter fit model (inset). The OD (mean corrected) is indicated on the Y-axis and the Hsp70 concentration (ng/ml) on the X-axis. (B) Linearity of the lipHsp70 ELISA was assessed by comparing first-, second- and third-order model fits of a relative concentration vs. system output plot. Linearity was shown within a concentration range of 0.36-17.4 ng/ml. (C) Recovery of free Hsp70 in buffer: 2.5 ng/ml Hsp70 was spiked into dilution buffer. The lipHsp70 ELISA recovered 2.53±0.09 ng/ml (left panel) and thus revealed a significantly better recovery (101±3%, right panel) compared to the control ELISA (1.43±0.07 ng/ml, left panel; 57±3%, right panel). The data show the mean of n=20 tests. (D) Recovery of free Hsp70 in serum: 2.5 ng/ml and 5 ng/ml Hsp70 were spiked into serum (diluted 1:5). The lipHsp70 ELISA recovered 1.98±0.12 ng/ml and 3.82±0.12 ng/ml for 2.5 and 5 ng/ml (left panel) and thus revealed a significantly better recovery (mean 78±3%, right panel) compared to the control ELISA (1.41±0.07 ng/ml and 2.18±0.09 ng/ml, left panel; mean 50±3%, right panel). Black bars: lipHsp70 ELISA, white bars: control ELISA, dashed line: expected amount of Hsp70. *$p<0.05$, ***$p<0.001$ (t-test).
Figure 2:
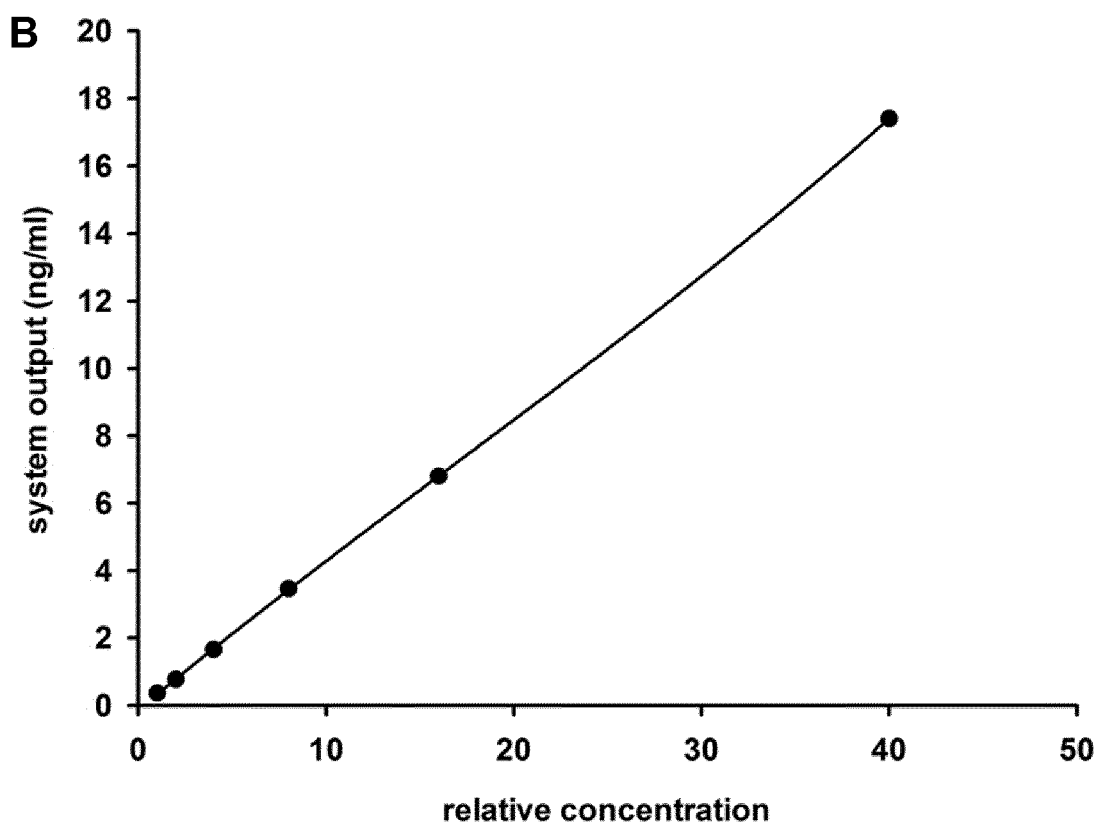
Figure 2:
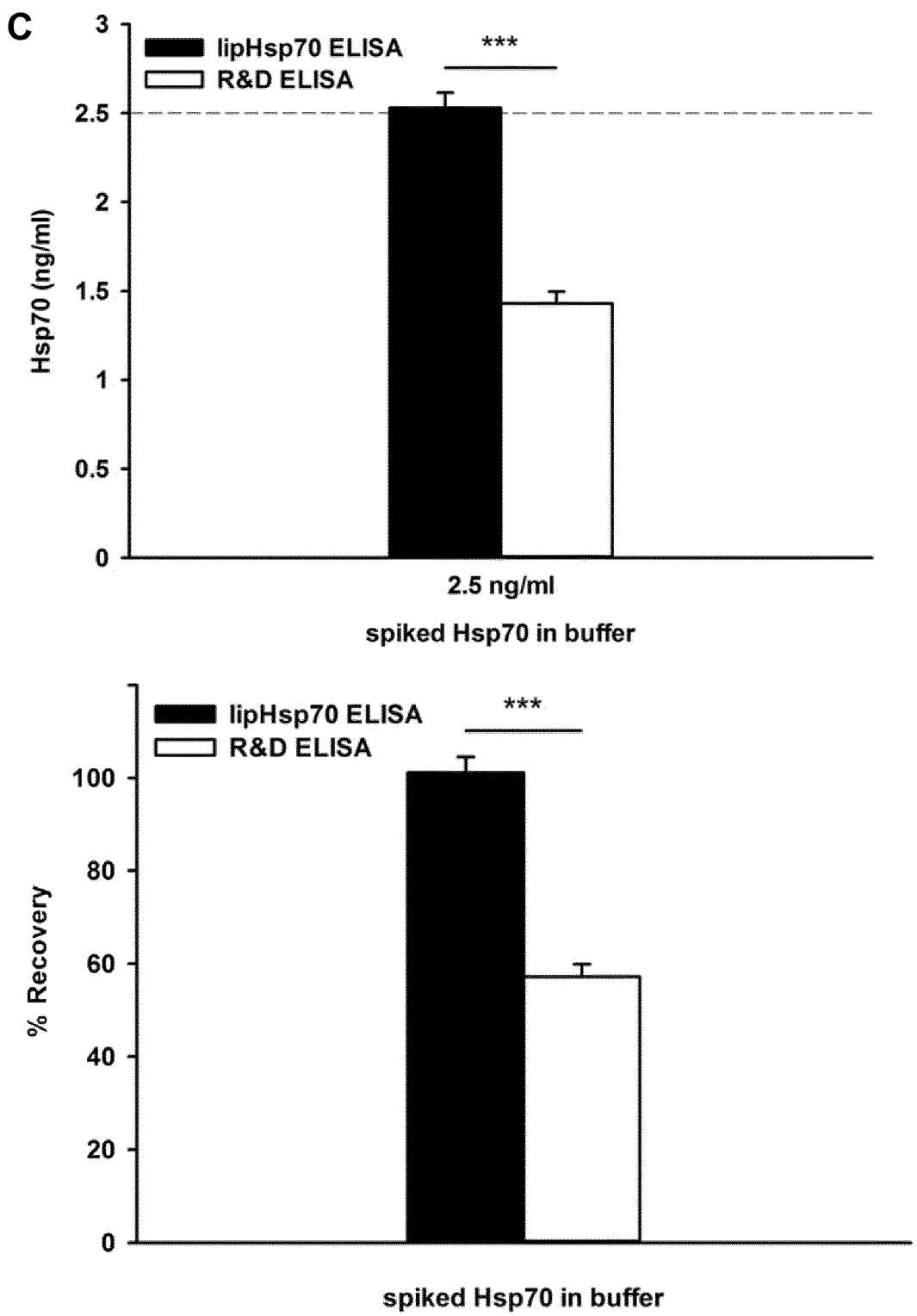
Figure 2:
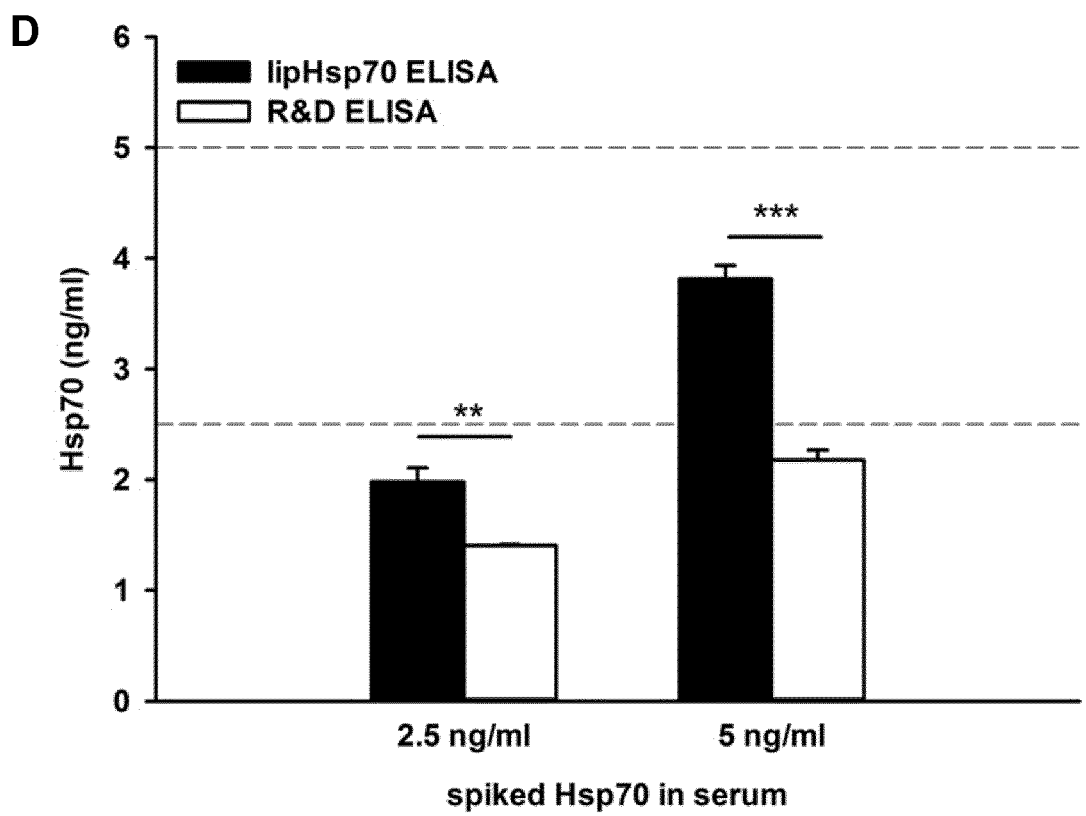
Figure 2:
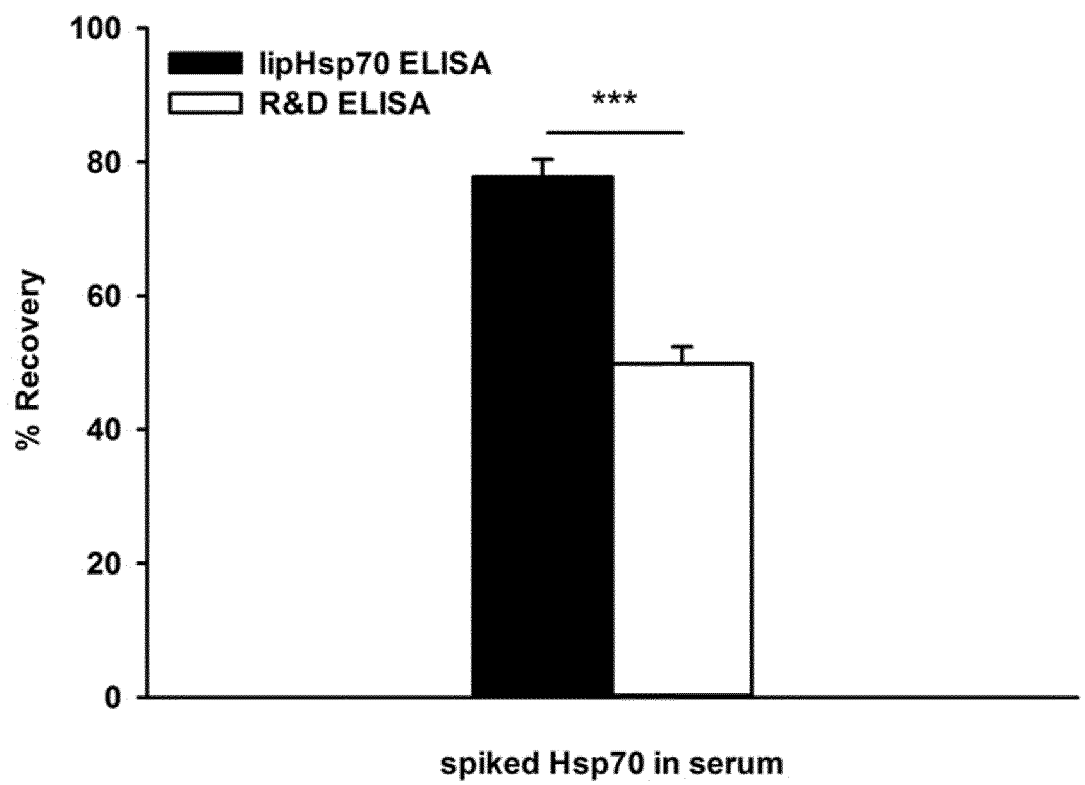
Figure 3:
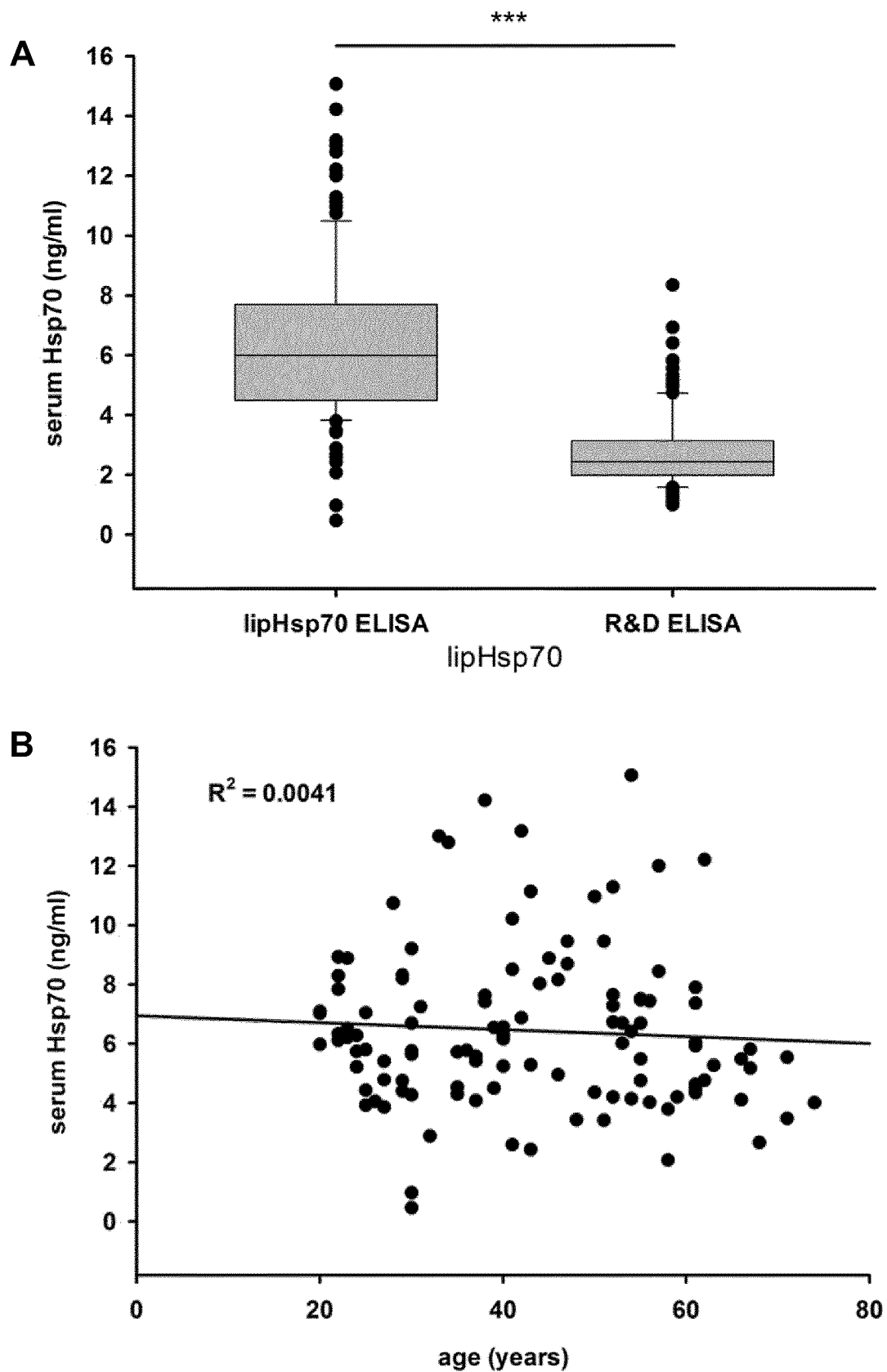
FIG. 3: Hsp70 serum levels in healthy human volunteers determined with the lipHsp70 and control Hsp70 ELISA. (A) Serum samples were taken from 114 healthy human volunteers and Hsp70 levels were determined comparatively with the lipHsp70 and the control Hsp70 ELISA (ctrl ELISA). The lipHsp70 ELISA detected significantly higher Hsp70 concentrations (6.4±2.7 ng/ml) in the serum than the ctrl ELISA (2.8±1.3 ng/ml). Lines inside the box plots show the median value, upper and lower boundaries indicate the 25th and the 75th percentile, whiskers indicate the 10th and the 90th percentile, respectively. ***$p<0.001$ (Mann-Whitney Rank Sum Test). (B) The Hsp70 serum levels determined with the lipHsp70 (upper panel) and the control ELISA (lower panel) showed no correlation with the age of the donors.
Figure 3:
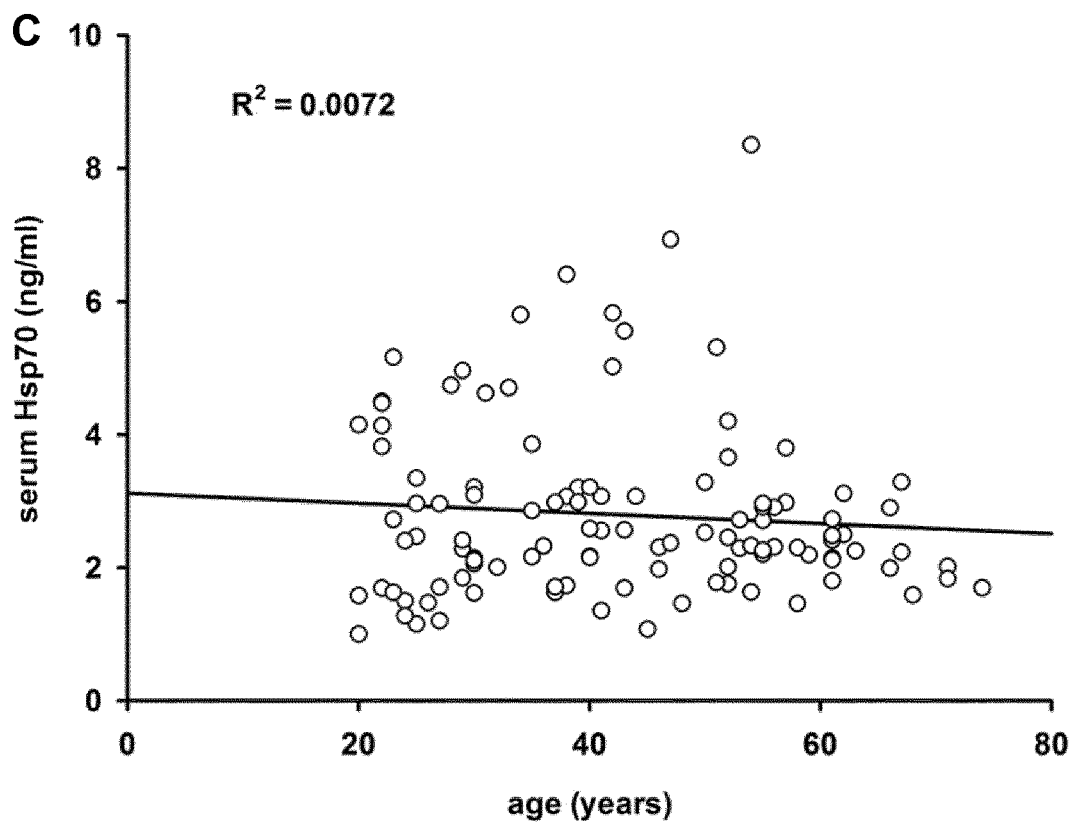

The present invention generally relates to a novel assay for the assessment of blood-borne biomarkers for the detection and diagnosis of tumors, including, but not limited to, human head and neck cancer, lung cancer, colorectal carcinoma, pancreatic cancer, glioblastoma and hematological malignancies as well as infectious or inflammatory disorders such as multiple sclerosis (MS). In accordance with the present invention, the practice of the detection and diagnosis of tumors, infections or inflammation is indicated by the presence and localization of certain markers in diseased tissue or cells. In particular, the present invention relates to a method of diagnosing a disease or condition associated with free and lipid-bound (exosomal) Hsp70, for example lipid-associated Hsp70 in exosomes and in the plasma membrane of living tumor cells, which in accordance with the present invention is reflected by an increased levels of lipid-bound (exosomal) Hsp70 and a specific conformational epitope of lipid-bound (exosomal) Hsp70, respectively, in a body fluid, in particular plasma or serum of the subject affected with the disease or condition. The findings of the present invention that the herein used anti-Hsp70 antibodies recognize a specific conformational epitope of lipid-bound (exosomal) Hsp70 further let to the development of a novel method for assaying free and lipid-bound (exosomal) Hsp70 in a sample derived from a body fluid of a subject, preferably an anti-Hsp70 antibody comprising determining the level of free and lipid-bound (exosomal) Hsp70 in a sample derived from a body fluid, preferably plasma or serum of the subject, wherein the increased level of Hsp70 in the sample of the subject compared to a control indicates the presence of or provides the opportunity to monitor a tumor, respectively, wherein the method is characterized in that the level of free and lipid-bound (exosomal) Hsp70 is determined by way of detecting a particular conformational epitope of Hsp70.

The above disclosure generally describes the present invention. Unless otherwise stated, a term as used herein is given the definition as provided in the Oxford Dictionary of Biochemistry and Molecular Biology, Oxford University Press, 1997, revised 2000 and reprinted 2003, ISBN 0 19 850673 2. Several documents are cited throughout the text of this specification. Full bibliographic citations may be found at the end of the specification immediately preceding the claims. The contents of all cited references (including literature references, issued patents, published patent applications as cited throughout this application including the background section and manufacturer's specifications, instructions, etc.) are hereby expressly incorporated by reference; however, there is no admission that any document cited is indeed prior art as to the present invention. Furthermore, for the avoidance of any doubt the technical content of the prior art referred to in the background section form part of the disclosure of the present invention and may be relied upon for any embodiment claimed herein. A more complete understanding can be obtained by reference to the following specific examples which are provided herein for purposes of illustration only and are not intended to limit the scope of the invention.

EXAMPLES

The Examples 1 to 7 which follow and corresponding FIGS. 1 to 8 further illustrate the invention, but should not be construed to limit the scope of the invention in any way.

Blood-borne biomarkers have potential utility for the detection of tumors, monitoring tumor growth and assessing the outcome of anti-tumor therapies [34-36], but many have been criticized for their lack of specificity and selectivity [37-39]. Although heat shock (stress) proteins are commonly considered as being intracellular molecules, elevated levels of Hsp70 have been detected in the supernatants of cultured tumor cells [16] and also in the peripheral circulation of patients with cancer and other diseases [40]. Levels of circulating heat shock proteins, including Hsp70 might therefore serve as useful biomarkers for disease in a number of clinical settings. Extracellular Hsp70 exists either as a free protein, as a protein in association with lipid vesicles such as exosomes [15] and lysosomal endosomes [41] or in the context of cholesterol-rich microdomains [42]. The minor part of extracellular Hsp70 is free Hsp70, which is mostly derived from dying cells. Only combined treatment modalities such as radiation plus hyperthermia have been shown to increase the release of free Hsp70 by dying cells [43]. The major proportion of extracellular Hsp70, which is derived from living, metabolically active tumor cells, is bound to small lipid vesicles such as exosomes, which are actively released by a large variety of human tumor cell types [8, 15]. Lipid-bound, exosomal Hsp70 could therefore be an interesting novel biomarker, which might better reflect the presence and size of viable tumor masses in patients and their response to treatment.

Figure 4:
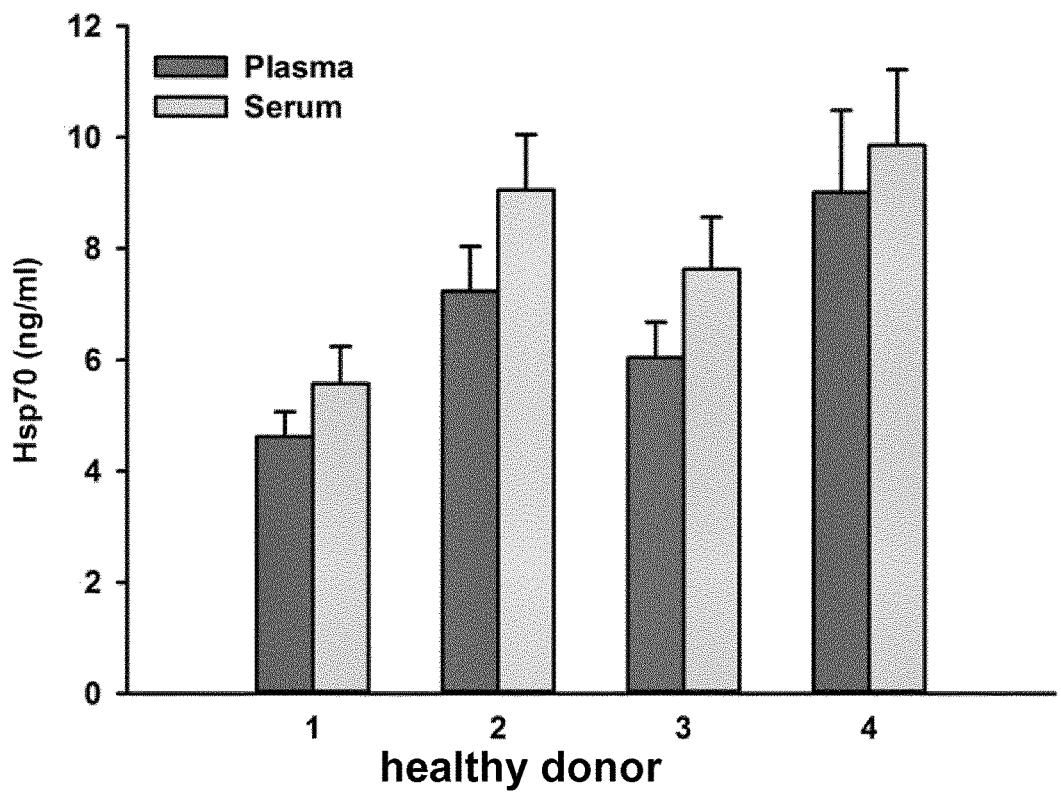
FIG. 4: Comparison of the detection of Hsp70 in serum and plasma. Plasma (black) and serum (grey bars) were taken in parallel from four healthy donors with different basal Hsp70 serum levels. No significant differences could be detected between the Hsp70 values derived from plasma and serum.
Figure 5:
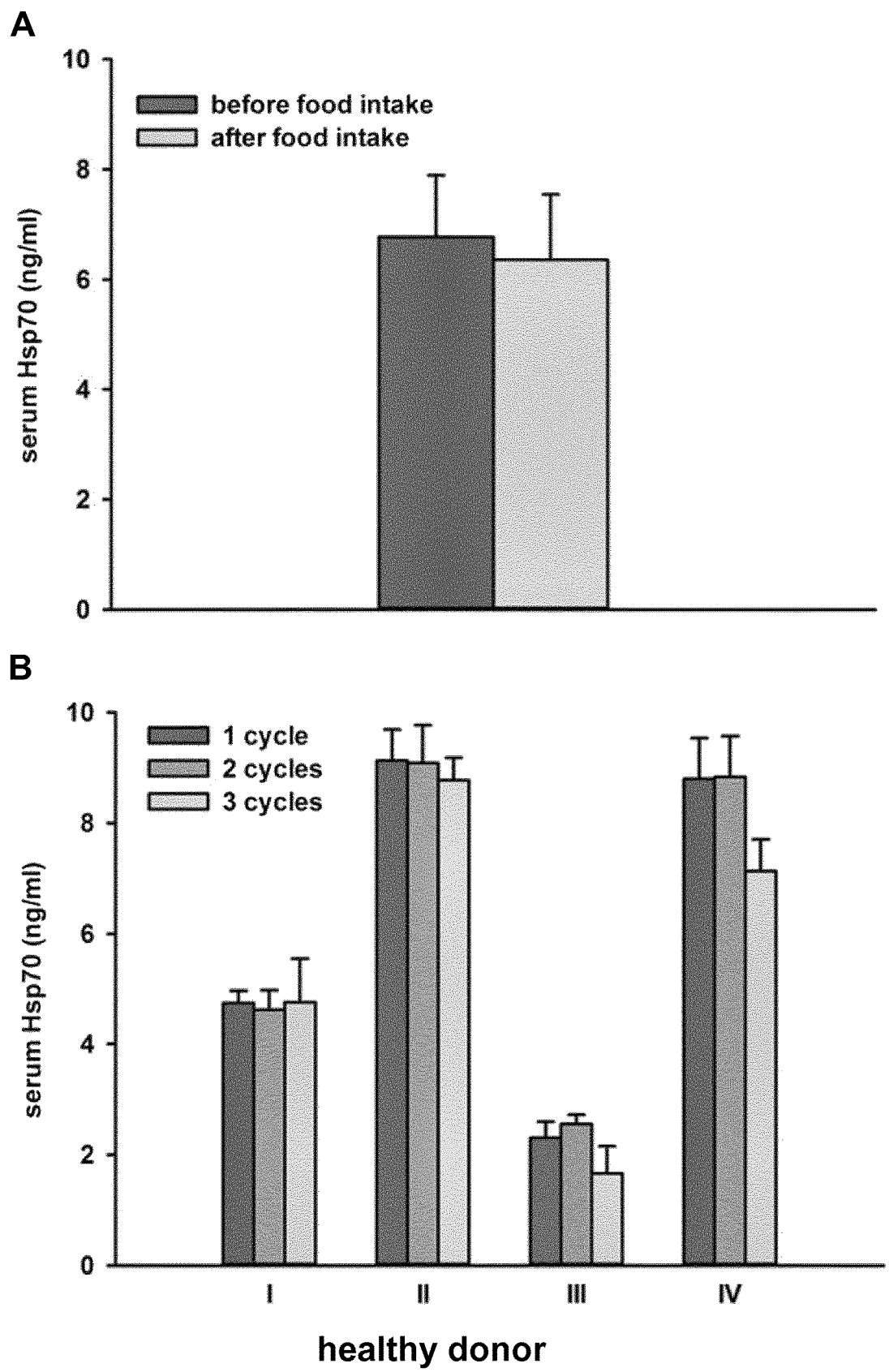
FIG. 5: Influence of interference factors on the detection of Hsp70 in serum using the lipHsp70 ELISA. (A) Serum samples of seven healthy individuals were taken before (dark grey bar) and two hours after intake of a high-fat diet (light grey bar). Hsp70 serum levels were determined using the lipHsp70 ELISA. No significant differences in the Hsp70 serum values were detected before and after food intake. (B) Serum samples were subjected to three repeated cycles of freezing and thawing and Hsp70 levels were determined after each cycle. No significant differences in the Hsp70 values were detected after repeated freezing and thawing using the lipHsp70 ELISA. (C) Serum samples were spiked with increasing amounts of lysed, autologous erythrocytes and Hsp70 levels were determined using the lipHsp70 ELISA (n=3). Up to a hemoglobin concentration of 9.6 mg/dl in the serum the Hsp70 values remained unaffected; higher serum hemoglobin concentrations resulted in a significant increase in the Hsp70 values. $p<0.01$, *$p<0.001$ (t-test).
Figure 5:
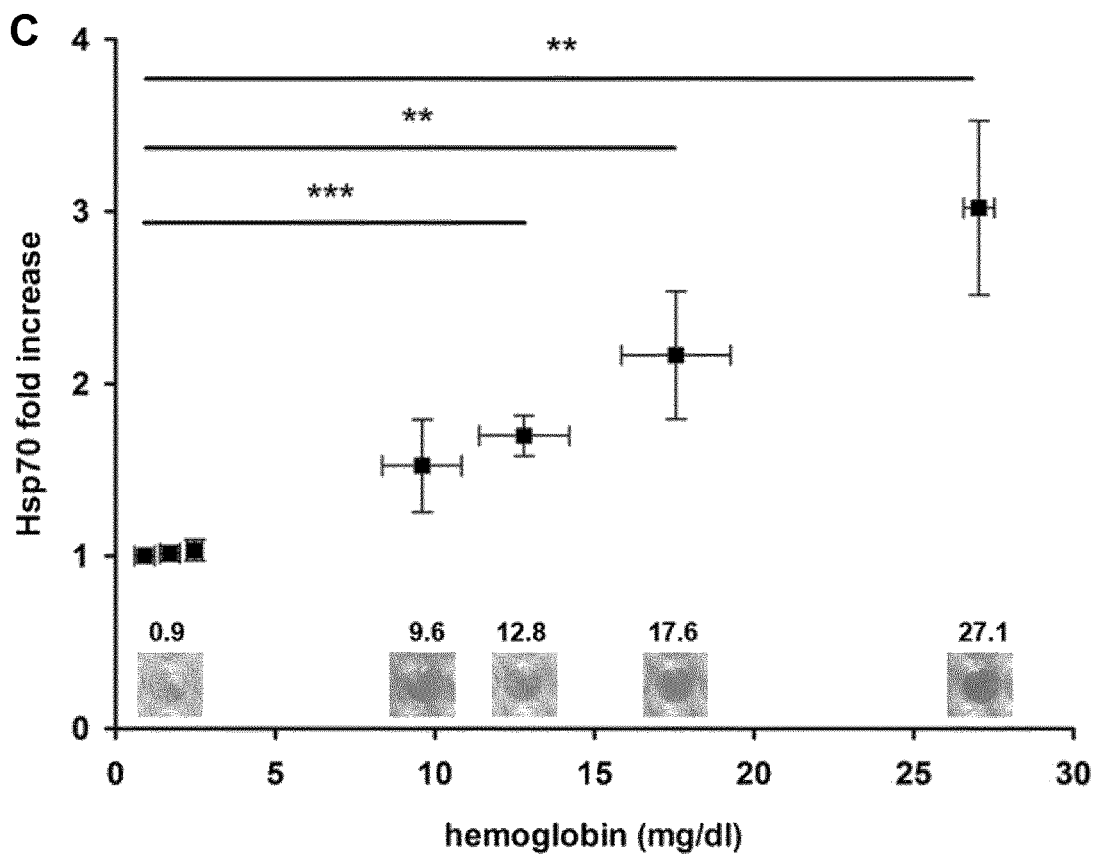
Figure 6:
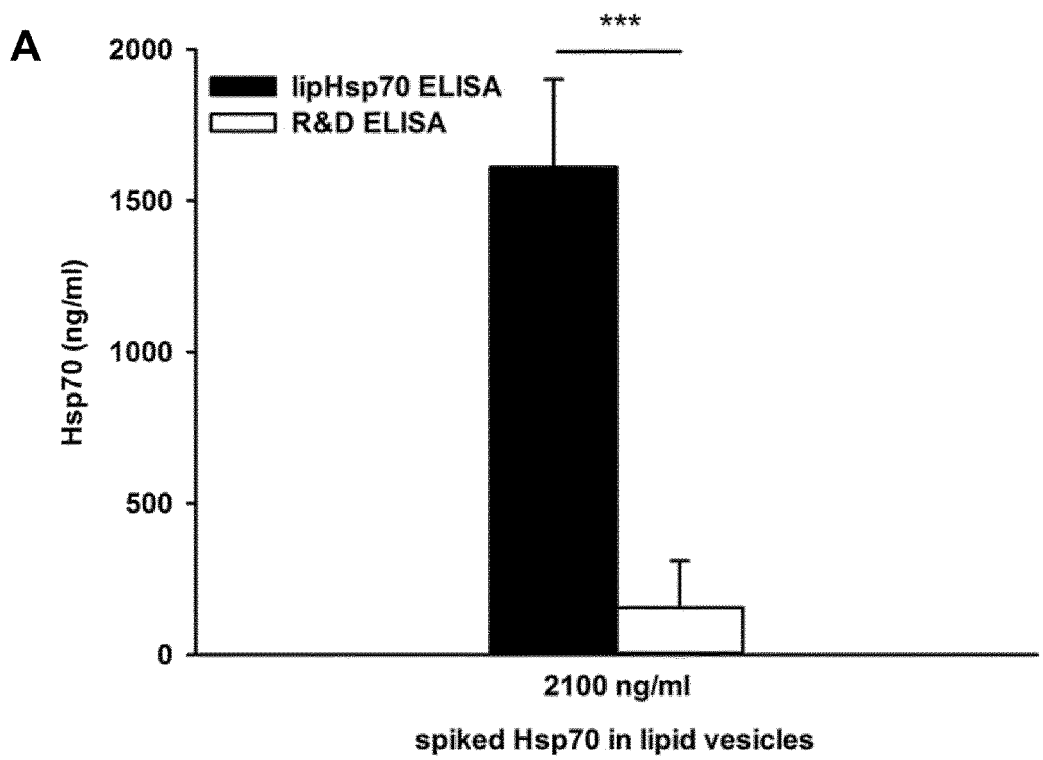
FIG. 6: Recovery of lipid-bound Hsp70 using the lipHsp70 ELISA and the control Hsp70 ELISA. Artificial POP S/POPC lipid vesicles were produced and loaded with recombinant Hsp70. Recovery of lipid-bound Hsp70: according to quantitative Western blot analysis (data not shown) the lipid vesicles were loaded with 2,100 ng/ml Hsp70. The lipHsp70 ELISA recovered 1,610±292 ng/ml (left panel) and thus revealed a significantly better recovery (76±5%, right panel) compared to the control ELISA (155±36 ng/ml, left panel; 7±1%, right panel). The data show the mean of n=3 tests. Black bars: lipHsp70 ELISA, white bars: control ELISA.***p<0.001 (t-test).
Figure 6:
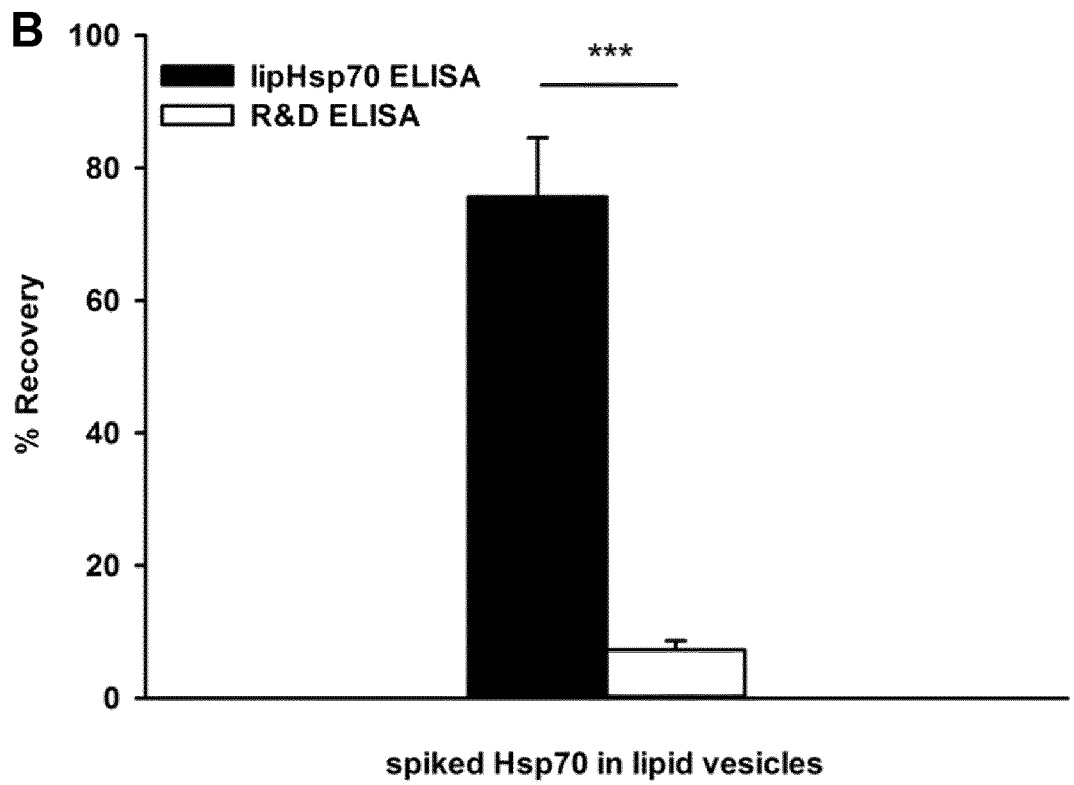
Figure 7:
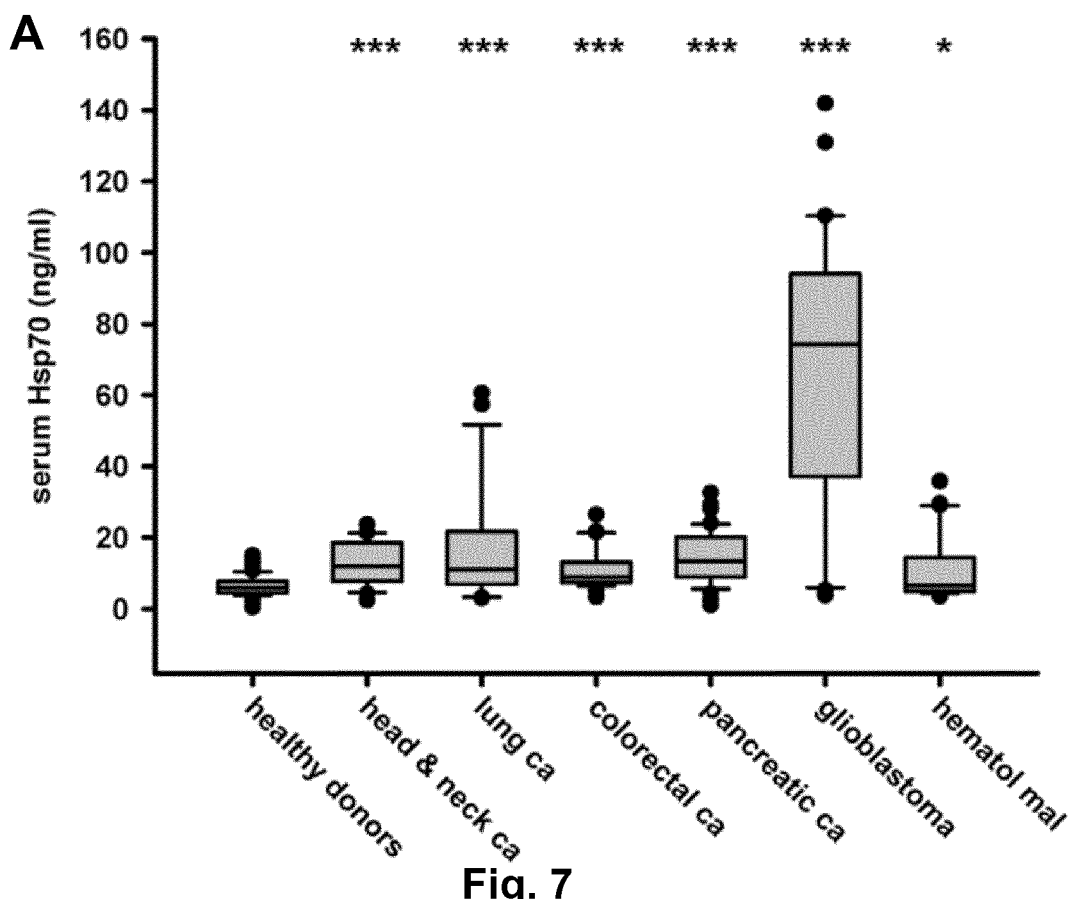
FIG. 7: Hsp70 serum levels in patients with different tumor entities compared to healthy controls. (A) Serum samples were taken from healthy human volunteers (n=114) and patients with squamous carcinomas of the head and neck (n=23), lung cancer (n=22), colorectal cancer (n=44), pancreatic cancer (n=46), glioblastoma (n=30) or haematological malignancies (n=32). Patient characteristics are summarized in Table 3. Significantly higher Hsp70 levels were found in all tumour patient cohorts compared to the healthy controls. Lines inside the box plots show the median value, upper and lower boundaries indicate the 25th and the 75th percentile, whiskers indicate the 10th and the 90th percentile, respectively. *p<0.05, ***p<0.001 (Mann-Whitney Rank Sum Test). (B) ROC curve analysis was performed on the data shown in (A). AUC, sensitivity and specificity data are summarized in Table 2.
Figure 7:
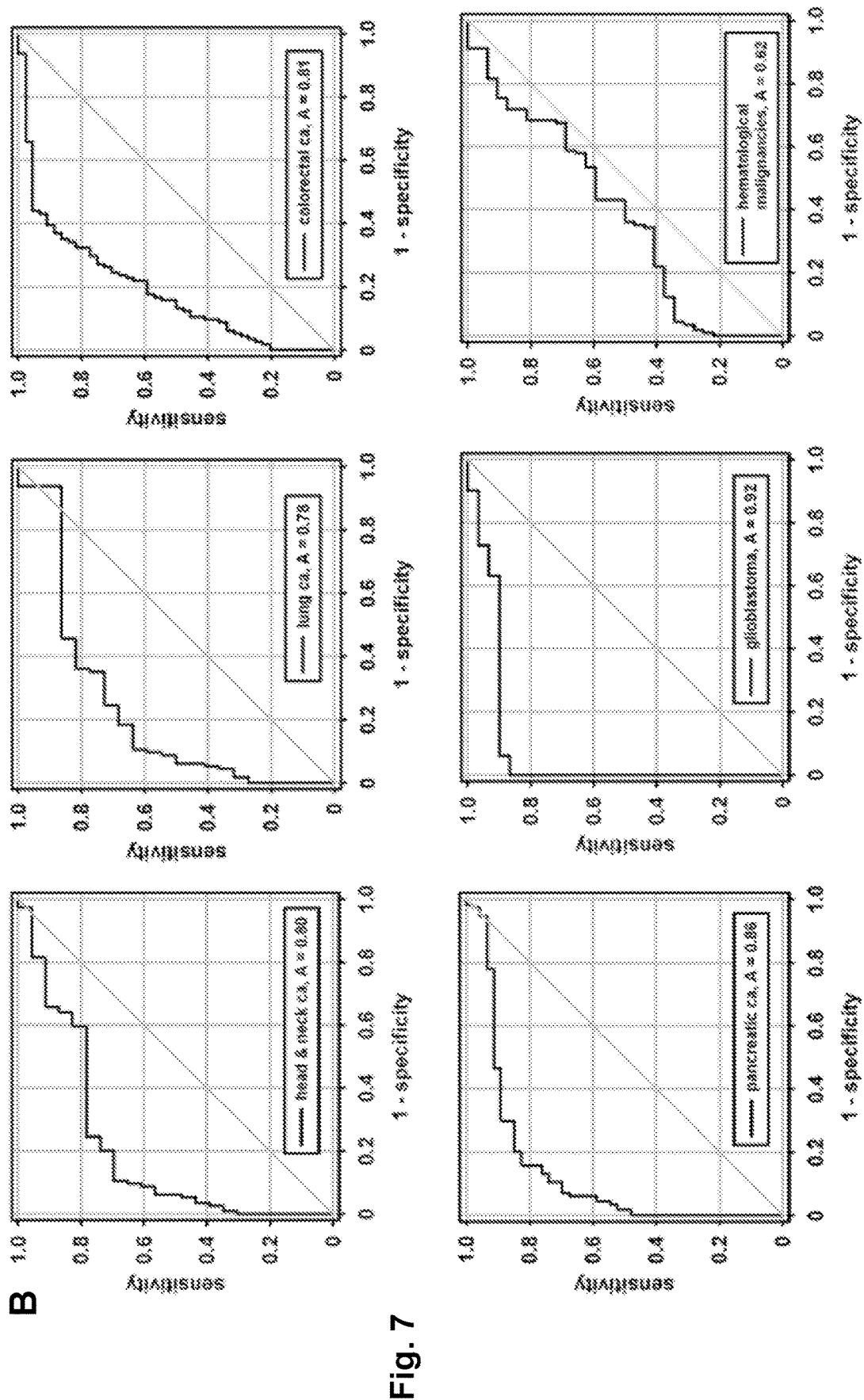
Figure 8:
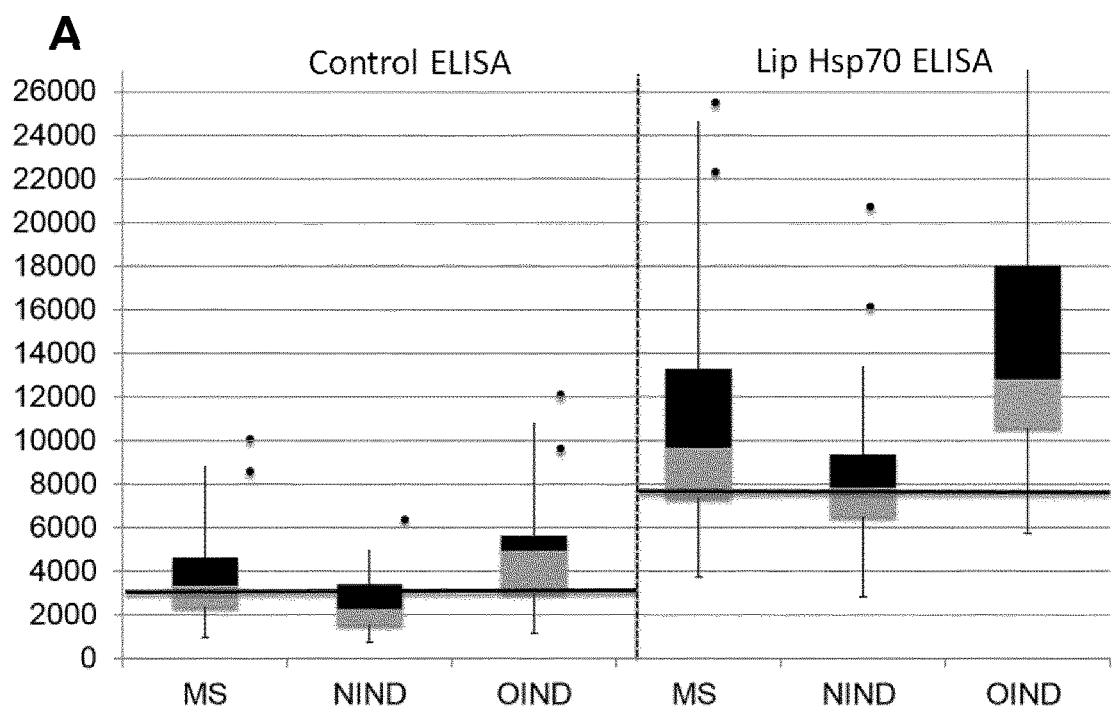
FIG. 8: Hsp70 serum levels in patients with multiple sclerosis (MS). (A) Comparison of the detection of Hsp70 with Control and Lip Hsp70 ELISA. Serum samples were taken from patients with Multiple Sclerosis (MS), non-inflammatory diseases (NIND) and other inflammatory diseases (OIND). The black line indicates the background level measured in healthy controls (n=100). (B) Comparison of the detection of Hsp70 with Control and Lip HSp70 ELISA. Serum samples were taken from patients with relapsing remitting Multiple Sclerosis (RRMS) and patients with non-relapsing remitting MS. The black line indicates the background level measured in healthy controls (n=100). (C) Summary of Hsp70-positive cases in multiple sclerosis. Patient characteristics are summarized in Tables 4A to 4C.
Figure 8:
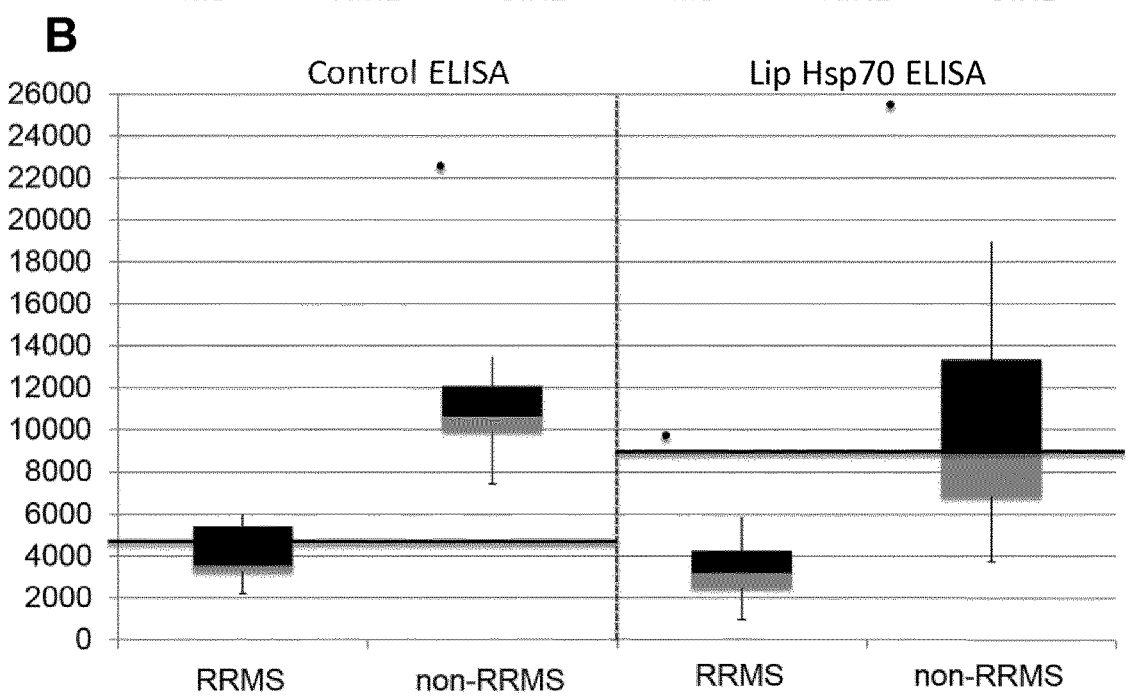
Figure 8:
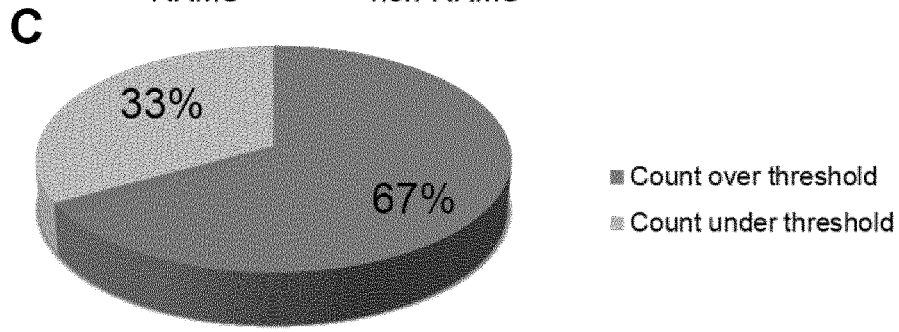

However, most commercially available Hsp70 ELISA systems are optimized and validated for the analysis of free Hsp70 protein in buffer systems, and it is therefore not too surprising that different "in-house" and commercially available Hsp70 assays have reported different Hsp70 levels [17-21]. A prerequisite for measuring the absolute levels of Hsp70 in patient blood is therefore an assay that reliably detects both free and liposomal Hsp70. The inventors of the present invention have previously reported on the development and validation of a mouse monoclonal antibody, which is able to bind to a form of Hsp70 that is selectively located in the plasma membrane of viable tumor cells (cmHsp70.1) [29], but also detects free Hsp70 in Western blots. This antibody was validated as a detection reagent for liposomal and free Hsp70 in the lipHsp70 ELISA, which is described in the following Examples. The lipHsp70 ELISA allows the quantification of Hsp70 in serum and plasma, and is less susceptible to matrix effects that are often caused by serum components as demonstrated in Examples 2-4 as well as in FIGS. 3 to 5. The validation experiments (summarized in Table 1) indicate high assay precision and linearity in the relevant concentration range. The recovery of spiked Hsp70 in buffer and serum samples was significantly higher with the lipHsp70 ELISA compared to that of a commercial ELISA as shown in Example 1 and FIG. 2. The most prominent differences in the recovery of Hsp70 were detected with respect to liposomal Hsp70, in that the lipHsp70 ELISA recovered tenfold more of the liposomal Hsp70 than the commercial ELISA. An explanation for this observation is a differential capacity of the monoclonal antibodies to recognize the lipid-associated form of Hsp70 as outlined schematically in FIG. 1. Membrane-bound Hsp70 is often located in detergent-resistant microdomains or lipid rafts [8, 44]. As most commercially available sample dilution buffers for ELISAs contain non-ionic detergents to dissolve lipid vesicles, it is likely that a proportion of serum Hsp70 remains associated with lipids after treatment (FIG. 1A). The continued association of Hsp70 with lipid components could inhibit the binding of Hsp70-specific antibodies that are used in commercial kits or influence the conformation of Hsp70 such that binding of the antibody does not occur. In contrast, the documented ability of the cmHsp70.1 antibody to detect the membrane-bound conformation of Hsp70 on viable tumor cells (FIG. 1B) suggests that it can also recognize lipid-associated Hsp70 as further shown in Example 5 and FIG. 6. Since a major proportion of serum-derived Hsp70 is bound to lipid vesicles, the lipHsp70 ELISA is more appropriate for the measurement of circulating Hsp70 that is derived from viable tumor cells. The basal levels of Hsp70 in the serum of 114 healthy human donors were found to be significantly higher with the lipHsp70 ELISA compared to the commercial ELISA as summarized in Table 1 and shown in Example 2 as wells as FIG. 3. The results obtained with the lipHsp70 ELISA remained unaffected by food intake of the blood donor and repeated freezing and thawing of the serum samples, thereby facilitating the use of this assay in the clinical setting as shown in Example 4 and FIG. 5. The lipHsp70 ELISA also tolerated moderate hemolysis up to a hemoglobin concentration of 9.6 mg/dl, with concentrations above this level resulting in a non-specific increase of the measured Hsp70 values (FIG. 5C). The higher Hsp70 levels in healthy donors that were measured with the lipHsp70 ELISA are most likely due to the fact that hematopoietic cells such as B cells, T cells, dendritic cells, mast cells and platelets, as well as intestinal epithelial cells, Schwann cells, neuronal cells, adipocytes and fibroblasts have all been reported to release exosomes that contain low amounts of Hsp70 in their lumen [25]. Furthermore, significantly higher Hsp70 levels were detected in the serum of patients with various different tumor entities compared to healthy controls, which is not too surprising given that tumor cells exhibit higher cytosolic Hsp70 levels and actively release high amounts of Hsp70 in lipid vesicles (Table 2). Notably, the inventors of the present invention observed distinct differences with elevated concentrations of circulating Hsp70 in patients with different tumor entities as shown in Example 6 as wells as FIG. 7. Although these data require future analysis and validation with extended cohorts of patients, these relationships may provide evidence on different expression patterns not only between individual patients but also between different tumor entities. In addition, significantly higher Hsp70 levels were detected in the serum of patients with infectious diseases such as EBV, HIV, Hepatitis B/C and patients with autoimmune diseases such as rheumatoid arthritis, SLE.

In summary, the reliability and robustness of the method of the present invention, in particular the lipHsp70 ELISA together with its ability to detect higher levels of Hsp70 in the circulation of patients with cancer and multiple sclerosis (MS) as demonstrated in the Examples and confirmed by Breuninger et al., J. Clin. Cell Immunol. 5 (2014), 264; Gunther et al., Front. Immunol. 6 (2015), 556 makes this method a promising tool for monitoring the presence and size of viable tumor mass, as well as therapeutic outcomes.

Detailed descriptions of conventional methods, such as those employed herein can be found in the cited literature; see also "The Merck Manual of Diagnosis and Therapy" Seventeenth Ed. ed. by Beers and Berkow (Merck & Co., Inc., 2003). The practice of the present invention will employ, unless otherwise indicated, conventional techniques of cell biology, cell culture, molecular biology, transgenic biology, microbiology, recombinant DNA, and immunology, which are within the skill of the art. For further elaboration of general techniques useful in the practice of this invention, the practitioner can refer to standard textbooks and reviews in cell biology and tissue culture; see also the references cited in the Examples. General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Non-viral Vectors for Gene Therapy (Wagner et al. eds., Academic Press 1999); Viral Vectors (Kaplitt & Loewy eds., Academic Press 1995); Immunology Methods Manual (Lefkovits ed., Academic Press 1997); and Cell and Tissue Culture: Laboratory Procedures in Biotechnology (Doyle & Griffiths, John Wiley & Sons 1998). Reagents, cloning vectors and kits for genetic manipulation referred to in this disclosure are available from commercial vendors such as BioRad, Stratagene, Invitrogen, Sigma-Aldrich, and ClonTech.

Material and Methods

Collection of Plasma and Serum Samples

Blood samples (9 ml) were taken from 114 healthy human volunteers and patients with head and neck cancer (n=23), lung cancer (n=22), colorectal cancer (n=44), pancreatic cancer (n=46), gliobastoma (n=30) or hematological malignancies (n=32), multiple sclerosis (MS, n=60) with relapsing remitting multiple sclerosis (RRMS, n=32), non-relapsing remitting multiple sclerosis (non-RRMS, n=19), SPMS (n=12), other inflammatory neurological diseases (OIND, n=18) non-inflammatory neurological diseases such as Alzheimer's disease, Parkinson's disease and Huntington's disease (NIND, n=22) who provided informed, written consent. Patient characteristics are summarized in tables 2 and 3. Blood was collected in one EDTA KE tube and one serum separator tube (S-Monovette, Sarstedt, Nümbrecht, Germany) and mixed by gently inverting the tube. For plasma separation, EDTA blood was centrifuged at 1,500 g for 15 min. For serum collection, blood was allowed to clot for 15 min at room temperature and serum was separated by centrifugation at 750 g for 10 min. Serum from leukemia patients was allowed to clot for two to three hours and separated by centrifugation at 380 g for 5 min. Serum and plasma were stored in 150 µl aliquots at −80° C. Approval of the study was obtained by the Ethics Committees of the universities that are involved in the study. All procedures were in accordance with the Helsinki Declaration of 1975 as revised in 2008. To validate the ELISA, the interference factors food intake of the blood donor, repeated freezing and thawing and hemolysis of the serum samples were tested. To test the influence of food intake, serum samples were collected from healthy human individuals before and 2 h after intake of a high-fat diet. Repeated freezing and thawing procedures of up to ten cycles were performed on the serum samples. In order to study the impact of hemolysis on the assay precision, erythrocytes were isolated from the blood of healthy donors by density gradient centrifugation using LSM1077 (PAA, Colbe, Germany). Erythrocytes were lysed by applying shear stress and the corresponding serum samples were spiked with increasing amounts of the lysed erythrocytes. The hemoglobin content of the spiked serum samples was analyzed by measuring the absorbance of the samples at 562 nm, 578 nm and 598 nm. The hemoglobin concentration was calculated as described elsewhere [30].

Recombinant Hsp70

His-tagged Hsp70 protein was isolated from a Sf9 insect cell system (Orbigen, San Diego, Calif., USA). Briefly, Sf9 cells were transfected with baculovirus containing cDNA coding for human Hsp70 protein with a His-tag on the N terminus (Orbigen, San Diego, Calif., USA). Cell lysates were loaded on Ni-sepharose columns (GE Healthcare, Chalfont St. Giles, UK) in binding buffer (20 mM sodium phosphate, 0.5 M NaCl, pH 7.4). His-tagged Hsp70 was eluted with increasing concentration of elution buffer (20 mM sodium phosphate, 0.5 M NaCl, 0.5 M imidazole, pH 7.4). Fractions containing high amounts of Hsp70 were pooled and the buffer was exchanged using PD-10 desalting columns (GE Healthcare, Chalfont St. Giles, UK). Protein amount was determined using a BCA protein kit (Pierce, Thermo, Rockford, Ill., USA) and aliquots were stored at −20° C. As a further control, recombinant Hsp70 without His-tag was purchased from Stressgen (ADI-NSP-555, Enzo Life Sciences, Farmingdale, N.Y., USA)

Antibody Biotinylation

The monoclonal mouse antibody cmHsp70.1 (multimmune, Munich, Germany) was biotinylated using EZ-link sulfo NHS-LC-biotin (Thermo, Rockford, Ill., USA). The antibody was incubated with a 40-fold molar excess of biotin for 1 h at room temperature. The remaining free biotin was removed using Zeba spin desalting columns (Thermo). Protein concentration was determined with a BCA protein kit (Pierce, Thermo) and aliquots were stored at 4° C.

Preparation of Lipid Vesicles

Lipid vesicles were prepared as described previously [31]. Briefly, 1-palmitoyl-2-oleoyl-sn-glycero-3-phosphocholine (POPC, Avanti Polar Lipids, Alabaster, Ala., USA) and 1-palmitoyl-2-oleoyl-sn-glycero-3-phospho-L-serine (POPS, Avanti Polar Lipids), dissolved in chloroform, were mixed in a molar ratio of 8:2 and dried under nitrogen gas. Lipids were rehydrated in 25 mM Tris/HCl pH 7.4, 250 mM NaCl at 10 mg lipid per 1 ml of buffer for 1.5 h at room temperature. The Mini Extruder (Avanti Polar Lipids) was assembled according to the manufacturer's instructions and the lipid suspension was pushed through a 100 nm polycarbonate membrane 13 times to achieve uniformly sized vesicles. Vesicle concentration was adjusted to 1 mg/ml with 1 mM Bis/Tris buffer pH 7.4 and 100 µl of the suspension were incubated with 1 µg of recombinant Hsp70 protein for 30 min at room temperature. After addition of an equal amount of ultrapure water the vesicle suspension was centrifuged at 200,000 g for 2 h at 4° C. in an ultracentrifuge. The pellet was resuspended in PBS and stored at 4° C. Hsp70-containing lipid vesicles and empty control vesicles were used for further tests within 24 hours.

SDS-PAGE and Western Blot Analysis

Lysed Hsp70-containing vesicles and defined concentrations of recombinant Hsp70 were loaded onto a 10% acrylamide gel under reducing conditions and blotted onto nitrocellulose membranes. The protein was detected using the monoclonal antibody cmHsp70.1 (multimmune, Munich, Germany). Bound antibodies were visualized using a horseradish peroxidase-conjugated secondary antibody (Dako, Glostrup, Denmark) and a chemiluminescence developing kit (Pierce, Thermo, Rockford, Ill., USA). The Hsp70 protein content of the vesicles was quantified by densitometry and compared to the signals generated by defined amounts of a recombinant Hsp70 protein that were run on the same gel.

LipHsp70 ELISA 96-well MaxiSorp Nunc-Immuno plates (Thermo, Rochester, N.Y.) were coated overnight with 2 µg/ml rabbit polyclonal antibody (Davids, Biotechnologie, Regensburg, Germany), directed against human recombinant Hsp70, in sodium carbonate buffer (0.1 M sodium carbonate, 0.1 M sodium hydrogen carbonate, pH 9.6). After washing three times with phosphate buffered saline (PBS, Life Technologies, Carlsbad, Calif., USA) with 0.05% Tween-20 (Calbiochem, Merck, Darmstadt, Germany), the wells were blocked with 2% milk powder (Carl Roth, Karlsruhe, Germany) in PBS for 1.5 h at 27° C. Following another washing step, serum samples diluted 1:5 in CrossDown Buffer (Applichem, Chicago, Ill., USA) were added to the wells for 2 h at 27° C. Then the wells were washed again and incubated with 4 µg/ml of the biotinylated mouse monoclonal antibody cmHsp70.1 (multimmune, Munich, Germany) in 2% milk powder in PBS for 2 h at 27° C. Finally, after another washing step, 0.2 µg/ml horseradish peroxidase-conjugated streptavidin (Pierce, Thermo, Rockford, Ill., USA) in 1% bovine serum albumin (Sigma-Aldrich, St. Louis, Mo., USA) was added for 1 h at 27° C. Binding was quantified by adding substrate reagent (R&D Systems, Minneapolis, Minn., USA) for 30 min at 27° C. and absorbance was read at 450 nm, corrected by absorbance at 570 nm, in a Microplate Reader (BioTek, Winooski, Vt., USA). An Hsp70 eight point standard was included into each ELISA test using 0-50 ng/ml recombinant Hsp70 diluted in CrossDown Buffer. As a control, Hsp70 serum levels were also determined using the DuoSet® IC Human/Mouse/Rat Total Hsp70 ELISA (R&D Systems, Minneapolis, Minn., USA) following the manufacturer's protocol.

ELISA Validation

Linearity was evaluated according to the Clinical Laboratory Standards Institute (CLSI) guideline EP6-A. Briefly, six solutions of different Hsp70 concentrations were analyzed with the ELISA and their relative concentration was plotted against the system output (concentration according to ELISA measurement). First-, second- and third-order models were then fitted to the data and a t-test was applied to the non-linear coefficients of the second- and third-order models using SigmaPlot 12.5 software. If none of the non-linear coefficients were significant (p>0.05), the dataset was considered linear. To determine intra-assay precision, control serum samples from two different donors were run in 20 replicates on a single plate. Inter-assay precision was assessed by running control serum samples in duplicate on three different days. The concentration was determined for each sample and the Co-efficients of Variation (CVs) were calculated. The Limit of Detection (LoD) was established according to the Clinical Laboratory Standards Institute (CLSI) guideline EP17-A as summarized by Armbruster and Pry [32]. Briefly, OD values of 36 blank samples and 36 samples with a low Hsp70 concentration (0.63 ng/ml) were converted to concentrations by back-calculating against the standard curve. The Limit of Blank (LoB) was calculated according to the following equation: $LoB = \mu + 1.645\sigma$, where $\mu$ and $\sigma$ are the mean and standard deviation of the blank measurements, respectively. Finally, the Limit of Detection (LoD) was calculated according to the following equation: $LoD = LoB + 1.645\, \sigma S$, where $\sigma S$ is the standard deviation of the low sample measurements. Recovery was assessed by spiking defined amounts of the respective standard Hsp70 into 1:5 diluted serum samples. The Hsp70 concentration of the serum alone was subtracted from the measured value and recovery was calculated as the ratio of observed concentration versus expected.

Deposit of Hybridoma Cell Lines

The material listed below was deposited with the DSMZ-Deutsche Sammlung von Mikroorganismen and Zellkulturen GmbH, Inhoffenstraße 7b formerly Mascheroder Weg 1b, D-38124 Braunschweig, Germany on Nov. 14, 2003, and assigned Accession Number DSM ACC2629 and DSM ACC2630. The deposits were made under the provisions of the Budapest Treaty on the International Recognition of Deposited Microorganisms for the Purposes of Patent Procedure and Regulations thereunder (Budapest Treaty). Maintenance of a viable culture is assured for thirty years from the date of deposit. The hybridomas have been made available by the DSMZ under the terms of the Budapest Treaty, and subject to an agreement between the applicant and the DSMZ which assures unrestricted availability of the deposited hybridomas and progeny thereof to the public upon issuance of a pertinent US and European patent; see EP 1 706 423 B1/B8, EP 2 070 947 B1, U.S. Pat. No. 7,700,737 B2 and U.S. Pat. No. 8,440,188 B2. The applicant of the present application has agreed that if a culture of the material(s) on deposit should die or be lost or destroyed when cultivated under suitable conditions, to replace the material(s) promptly upon notification with another of the same.

i. Hybridoma: cmHsp70.1, Date: Nov. 14, 2003, Accession Number DSM ACC2629
ii. Hybridoma: cmHsp70.2, Date: Nov. 14, 2003, Accession Number DSM ACC2630

Example 1

Hsp70 ELISA Validation: Calibration Curve, Intra- and Inter-Assay Precision, Limit of Detection and Recovery Hsp70 is frequently overexpressed in tumor cells and can be actively released in lipid vesicles by viable tumor cells. Therefore, elevated Hsp70 serum levels have potential utility as biomarkers for the detection of viable tumor mass and to measure the response to therapeutic interventions. However, commercially available Hsp70 ELISAs are neither optimized for the measurement of serum Hsp70 nor of lipid-associated Hsp70. Therefore, for the novel lipHsp70 ELISA, blocking reagents, antibody combinations and serum diluent had to be optimized. A 1:5 dilution of the serum samples was found to be optimal to reduce unfavorable matrix effects, which are observed with undiluted serum. As an internal control, a commercial ELISA was used in parallel. A representative calibration curve with eight measuring points and the fitting equation are shown in FIG. 2A. A four-parameter fit model was applied to obtain the function describing a sigmoid curve. In 20 independent experiments, the highest concentration of the standard yielded a mean OD value of 2.82 and a standard deviation of 0.34. Linearity was assessed by comparing linear and nonlinear polynomial fitting of the relationship between true and observed concentrations of six Hsp70 samples. The lipHsp70 ELISA was linear in a concentration range from 0.36-17.41 ng/ml (FIG. 2B). To determine assay precision, intra- and inter-assay runs were performed with control serum samples from two and five healthy donors, respectively, and the Co-efficients of Variation (CVs) were calculated. Intra-assay precision CVs ranged from 5.2% to 8.1%, and inter-assay precision CVs varied between 1.0% and 18.0% with a mean of 10.9%. The Limit of Detection (LoD) for the lipHsp70 ELISA was 0.3 ng/ml. Recovery was determined by spiking recombinant Hsp70 protein in buffer and serum samples using either the lipHsp70 or the commercially available ELISA as a control. When 2.5 ng/ml Hsp70 protein from Enzo Life Sciences were spiked into dilution buffer, the lipHsp70 ELISA recovered significantly higher amounts of the expected Hsp70 protein (2.53±0.09 ng/ml, 101±3% recovery) compared to the control ELISA (1.43±0.07 ng/ml, 57±3% recovery) (FIG. 2C). To determine the recovery of Hsp70 in serum samples, Hsp70 (2.5 ng/ml and 5 ng/ml) of the respective standards was spiked into serum samples derived from four different healthy volunteers. With an average recovery of 78±3%, the lipHsp70 ELISA showed a significantly higher recovery of the spiked Hsp70 compared to the control ELISA with 50±3% (FIG. 2D). The details of the assay performance are summarized in Table 1.

TABLE 1

Assay performance characteristics of the lipHsp70 ELISA.

| Parameters | Performance |
| --- | --- |
| Linear range (ng/ml) | 0.36-17.41 |
| Intra-assay precision (% CV) | 5.2-8.1 |
| Inter-assay precision (% CV) | 1.0-18.0 |
| Recovery (%): Buffer/Serum | 101 ± 3/78 ± 3 |
| Limit of Detection (ng/ml) | 0.31 |

Example 2

Hsp70 Serum Levels in Healthy Human Volunteers

Serum samples from 114 healthy human volunteers at different ages (age range 20-74, Table 2) were analyzed to determine the basal Hsp70 levels in blood. To minimize matrix effects, serum was diluted 1:5 in CrossDown Buffer prior to analysis. Significantly higher basal levels (6.4±2.7 ng/ml) could be detected with the lipHsp70 ELISA compared to the control ELISA (2.8±1.3 ng/ml) (FIG. 3A). The 25th and 75th percentiles were 4.5 ng/ml and 7.7 ng/ml for the lipHsp70 ELISA and 2.0 ng/ml and 3.1 ng/ml for the control ELISA, respectively. As shown in FIG. 3B, no correlation was found between the basal Hsp70 serum levels and the age of the donors using both ELISAs.

Example 3

Comparison of the Detection of Hsp70 in Serum and Plasma

To test whether the lipHsp70 ELISA is suitable for measuring Hsp70 levels in both serum and plasma, samples were taken in parallel from four healthy donors and measured using the lipHsp70 ELISA. For this experiment, donors with different basal levels of Hsp70 were chosen. For all four donors, the Hsp70 levels in plasma did not differ significantly from those in the corresponding serum samples. These data indicate that both serum and plasma can be used to measure Hsp70 levels with the lipHsp70 ELISA (FIG. 4).

Example 4

Influence of Interference Factors on the Detection of Hsp70

Different factors in the donor's lifestyle or in the sample preparation could have an impact on the measurement of Hsp70 in serum [33]. In order to determine the robustness of the lipHsp70 ELISA, the influence of food intake of the donor, repeated freezing and thawing of the serum sample and hemolysis was tested. Serum samples from seven healthy individuals were taken before and two hours after intake of a high-fat diet. In all donors, Hsp70 serum levels did not differ significantly before and after food intake (FIG. 5A). Serum samples from four healthy individuals with different basal levels of Hsp70 (2.3-9.1 ng/ml with the lipHsp70 ELISA and 1.4-2.1 ng/ml with the control ELISA) were subjected to three cycles of freezing and thawing and Hsp70 levels were determined after each cycle (FIG. 5B). Even after ten cycles, the measured Hsp70 values did not change significantly (data not shown). To test the influence of free hemoglobin in serum on the ELISA measurements, serum derived from three healthy individuals was spiked with increasing amounts of lysed erythrocytes. The hemoglobin content of the samples was analyzed and correlated with the measured Hsp70 levels. Free hemoglobin at a concentration of up to 9.6 mg/dl did not significantly change the measured Hsp70 values. In contrast, hemoglobin concentrations above 9.6 mg/dl resulted in a non-specific increase of the Hsp70 values (FIG. 5C).

Example 5

Detection of Lipid-Bound Hsp70

To test the ability of both ELISA tests to measure lipid-bound Hsp70, artificial POPS/POPC lipid vesicles were produced and loaded with recombinant Hsp70. The amount of lipid-associated Hsp70 that was determined with the lipHsp70 ELISA showed an excellent correlation with the Hsp70 concentration that was determined by Western blotting (data not shown). However, a comparison of the levels of liposomal Hsp70 using the lipHsp70 ELISA and the control ELISA revealed large differences. The recovery of liposomal Hsp70 using the lipHsp70 ELISA was 76±5%, whereas that of the control ELISA was only 7±1%. These data indicate that the detection of lipid-associated Hsp70 was more than 10-fold better with the lipHsp70 ELISA than with the control ELISA (FIGS. 6A, B).

Example 6

Hsp70 Serum Levels in Patients With Different Tumor Entities

Hsp70 levels were measured in the serum of patients with head and neck cancer (n=23), lung cancer (n=22), colorectal cancer (n=44), pancreatic cancer (n=46), glioblastoma (n=30) or hematological malignancies (n=32) (Table 3A-F) and compared to the Hsp70 levels in healthy donors (n=114). The mean Hsp70 serum levels in patients of all tumor entities were significantly higher than those of the healthy donors (FIG. 7A). Receiver Operating Characteristic (ROC) curve analysis was performed by comparing serum Hsp70 levels of healthy donors with those of the different patient cohorts (FIG. 7B). The Area Under the Curve (AUC; CI 95%) and sensitivity for a cut-off value of 7.7 ng/ml (derived from the 75th percentile of the healthy donors) is summarized in Table 2. The specificity was 75% for all patient groups.

Example 7

Hsp70 Serum Levels in Patients With Multiple Sclerosis, Non-Inflammatory Neurological Diseases and Other Inflammatory Neurological Diseases Hsp70 levels were measured in the serum of patients with Multiple Sclerosis (MS, n=53), non-inflammatory neurological diseases (NIND; n=21) and other inflammatory neurological diseases (OIND, n=16) (Table 4A-C) and compared to the Hsp70 levels in healthy donors (n=100) using a commercially available Hsp70 ELISA as internal control and the lipHsp70 ELISA. The mean Hsp70 serum levels in patients of MS and OIND were significantly higher than those of the patients with NIND and the healthy donors. Furthermore, a comparison of the levels of liposomal Hsp70 using the lipHsp70 ELISA and the control ELISA revealed large differences. The recovery of liposomal Hsp70 using the lipHsp70 ELISA in patients with MS NIND and with OIND were 85±5%, whereas that of the control ELISA was only 32±9%, (FIG. 8A). Furthermore, the Hsp70 levels were measured in the serum of patients with relapsing-remitting Multiple Sclerosis (RRMS, n=32) versus non-relapsing-remitting (non-RRMS, n=19) and compared to the Hsp70 levels in healthy donors (n=100) using a commercially available Hsp70 ELISA as internal control and the lipHsp70 ELISA. The mean Hsp70 serum levels in patients of non-RRMS were significantly higher than those of the patients with RRMS and the healthy donors. The recovery of liposomal Hsp70 using the lipHsp70 ELISA in patients with non-RRMS and RRMS was 87±5% whereas that of the control ELISA was only 28±10% (FIG. 8B). In summary, a comparison of the levels of liposomal Hsp70 using the herein disclosed lipHsp70 ELISA and the control ELISA revealed large differences, whereas 67% Hsp70 positive cases in MS could be identified when using the lipHsp70 ELISA (FIG. 8C).

TABLE 2

Age, gender and Hsp70 levels of healthy donors and patients.

|  |  | Healthy donors | Head & neck cancer | Lung cancer | Colorectal carcinoma | Pancreatic cancer | Glioblastoma | Hematological malignancies |
|---|---|---|---|---|---|---|---|---|
| Number (n) |  | 114 | 23 | 22 | 44 | 46 | 30 | 32 |
| Gender (M/F) |  | 67/47 | 21/2 | 16/6 | 26/18 | 26/20 | 14/16 | 25/7 |
| Age | Mean | 42.9 | 62.5 | 66.1 | 64.2 | 69.8 | 56.2 | 41.7 |
|  | Range | 20-74 | 36-83 | 48-88 | 29-81 | 44-90 | 25-77 | 19-64 |
|  | SD | 14.6 | 12.2 | 10.3 | 13.0 | 40.6 | 14.1 | 12.2 |
|  | Median | 41.5 | 61.0 | 66.5 | 67.5 | 73.0 | 59.0 | 42.0 |
| lipHsp70 ELISA | Mean Hsp70 (ng/ml) | 6.4 | 12.4 | 16.8 | 11.0 | 14.8 | 67.6 | 11.1 |
|  | SD | 2.7 | 6.1 | 16.2 | 5.2 | 7.3 | 37.5 | 9.0 |
| ROC | AUC (CI 95%) | — | 0.80 | 0.78 | 0.81 | 0.86 | 0.92 | 0.62 |
|  | p-value | — | <0.0001 | <0.0001 | <0.0001 | <0.0001 | <0.0001 | 0.03 |
|  | Sensitivity (%) | — | 78 | 73 | 70 | 85 | 90 | 41 |
|  | Specificity (%) | — | 75 | 75 | 75 | 75 | 75 | 75 |

Abbreviations:
AUC: Area Under the Curve;
M: Male;
F: Female;
CI: Confidence Interval;
ROC: Receiver Operating Characteristic;
SD: Standard Deviation

TABLE 3A

Clinico-pathological characteristics of head and neck cancer patients.

| Patient # | Tumor location | Histology | Staging | | | Grading |
|---|---|---|---|---|---|---|
| 1 | hypopharynx | SCCHN | T1 | N0 | M0 | G2 |
| 2 | hypopharynx | SCCHN | T3 | N2b | M0 | G3 |
| 3 | hypopharynx | SCCHN | T1 | N0 | M0 | G3 |
| 4 | larynx | SCCHN | T3 | N2 | M0 | G2 |
| 5 | larynx | SCCHN | T3 | N0 | M0 | G3 |
| 6 | larynx | SCCHN | T4 | N1 | M0 | G3 |
| 7 | larynx | SCCHN | T3 | N0 | M0 | G2 |
| 8 | larynx | SCCHN | T4a | N0 | M0 | G3 |
| 9 | naso/oro/hypo pharynx | SCCHN | T4c | N2c | M0 | G2 |
| 10 | naso/oro/hypo pharynx | SCCHN | T3-4a | N2c | M0 | G3 |
| 11 | nasopharynx | SCCHN | T2 | N0 | M0 | G1 |
| 12 | oral cavity | SCCHN | T1 | N0 | M0 | G2 |
| 13 | oro/hypopharynx | SCCHN | T2 | N2b | M0 | G3 |
| 14 | oro/hypopharynx | SCCHN | T2 | N2a | M0 | G2 |
| 15 | oropharynx | SCCHN | T4a | N2c | M0 | G3 |
| 16 | oropharynx | SCCHN | T3 | N0 | M0 | G3 |
| 17 | oropharynx | SCCHN | T1 | N2b | M0 | G2 |
| 18 | oropharynx | SCCHN | T1a | N0 | M0 | G2 |
| 19 | oropharynx | SCCHN | T4 | N0 | M0 | G2 |
| 20 | oropharynx | SCCHN | T2 | N2b | M0 | G3 |
| 21 | oropharynx | SCCHN | T4 | N0 | M0 | G3 |
| 22 | oropharynx | SCCHN | T2 | N1 | M0 | G3 |
| 23 | paranasal sinus | SCCHN | T2 | N0 | M0 | G3 |

Abbreviations:
SCCHN: Squamous Cell Carcinoma of the Head and Neck

TABLE 3B

Clinicopathological characteristics of lung cancer patients.

| Patient # | Histology | Histology | Staging | | | Grading |
|---|---|---|---|---|---|---|
| 1 | NSCLC adeno | SCCHN | T2 | N2 | M1 | G3 |
| 2 | NSCLC adeno | SCCHN | T4 | N2 | M0 | G2 |
| 3 | NSCLC adeno | SCCHN | T2 | N2 | M0 | G3 |
| 4 | NSCLC adeno | SCCHN | T3 | N3 | M1 | G3 |
| 5 | NSCLC adeno | SCCHN | T4 | N2 | M1 | G3 |
| 6 | NSCLC adeno | SCCHN | T2 | N0 | M0 | G2 |
| 7 | NSCLC adeno | SCCHN | T1 | N3 | M0 | G3 |
| 8 | NSCLC adeno | SCCHN | T2 | N2 | M1 | G2 |
| 9 | NSCLC squamous | SCCHN | T3 | N3 | M1 | G3 |
| 10 | NSCLC squamous | SCCHN | T3 | N3 | M1 | G3 |
| 11 | NSCLC squamous | SCCHN | T4 | N0 | M0 | G2 |
| 12 | NSCLC squamous | SCCHN | T1 | N0 | M0 | G3 |
| 13 | NSCLC squamous | SCCHN | T4 | N2 | M0 | G3 |
| 14 | NSCLC squamous | SCCHN | T4 | N3 | M1 | G3 |
| 15 | NSCLC squamous | SCCHN | T3 | N3 | M0 | G3 |
| 16 | NSCLC squamous | SCCHN | T3 | N2 | M1 | G3 |
| 17 | NSCLC squamous | SCCHN | T4 | N2 | M1 | G3 |
| 18 | NSCLC squamous | SCCHN | T3 | N2 | M1 | G2 |
| 19 | SCLC | SCCHN | limited | | | — |
| 20 | SCLC | SCCHN | extensive | | | — |
| 21 | SCLC | SCCHN | extensive | | | — |
| 22 | SCLC | SCCHN | extensive | | | — |

Abbreviations:
NSCLC: Non-Small Cell Lung Cancer;
SCLC: Small Cell Lung Cancer

TABLE 3C

Clinico-pathological characteristics of colorectal carcinoma patients.

| Patient # | Staging | | | Grading |
|---|---|---|---|---|
| 1 | uT3 | uN+ | MX | G2 |
| 2 | uT3 | uN0 | cM0 | G2 |
| 3 | cT3 | cN+ | cM0 | G2 |
| 4 | cT3 | cN1 | cM0 | G2 |
| 5 | cT3 | cN1 | cM1 | G2 |
| 6 | cT3 | cN0 | cM0 | G2 |
| 7 | cT3 | cN0 | cM0 | G2 |
| 8 | uT3 | uN0 | cM0 | G2 |
| 9 | cT3 | cN2 | cM0 | G2 |
| 10 | cT3 | uN0/cN+ | M0 | |
| 11 | cT3 | cN+ | cM0 | G2 |
| 12 | uT3 | cNX | cM0 | G2 |
| 13 | cT3 | cN1 | cM0 | G2 |
| 14 | uT3 | uN1 | cM0 | G2 |
| 15 | uT3 | cN0 | cM0 | G2 |
| 16 | cT2 | cN1 | cM0 | G2 |
| 17 | cT3 | cN2 | MX | G2 |
| 18 | cT3 | cN2 | cM0 | G2 |
| 19 | cT3a | cN2 | cM0 | |
| 20 | cT3-4 | cN+ | cM0 | G2 |

TABLE 3C-continued

Clinico-pathological characteristics of colorectal carcinoma patients.

| Patient # | Staging | | | Grading |
|---|---|---|---|---|
| 21 | cT3 | cN0 | cM0 | G2 |
| 22 | cT3 | cN1 | cM0 | G3 |
| 23 | uT3c | N0 | cM0 | G2 |
| 24 | uT3 | uN0 | cM0 | G2 |
| 25 | cT4 | cN1 | cM0 | G2 |
| 26 | uT3 | uN2 | cM0 | G2 |
| 27 | uT3 | uN1 | cM0 | G2 |
| 28 | u13 | uN1 | cM0 | G2 |
| 29 | uT3 | N+ | cM0 | G2 |
| 30 | cT3 | cN0 | cM0 | |
| 31 | cT3 | cN1 | cM0 | G2 |
| 32 | cT3 | cN2 | cM1 | G2 |
| 33 | T3 | N2 | M0 | G2 |
| 34 | cT3 | cN0 | M0 | G2 |
| 35 | uT3 | uN0 | cM0 | |
| 36 | cT3 | cN+ | cM0 | |
| 37 | cT3 | cN0 | cM0 | |
| 38 | cT2 | uN0 | M0 | G2 |
| 39 | cT3 | cN+ | cM0 | G2 |
| 40 | uT3 | uN1 | cM0 | G2 |
| 41 | uT3b-4 | cN+ | cM0 | |
| 42 | uT3 | uN1 | cM0 | G2 |
| 43 | cT3 | cN+ | cM0 | G2 |
| 44 | cT3 | uN1 | cM0 | G2 |

Abbreviations:
C: Staging by Clinical Examination;
u: Staging by Ultrasonography

TABLE 3D

Clinico-pathological characteristics of pancreatic cancer patients.

| Patient # | Tumor Location | Staging | | | Grading |
|---|---|---|---|---|---|
| 1 | body | T3 | N0 | M0 | G2 |
| 2 | body/tail | T2 | N1 | M1 | — |
| 3 | body/tail | T4 | N2 | M1 | — |
| 4 | body/tail | T4 | N2 | M1 | — |
| 5 | body/tail | T1 | N1 | M1 | — |
| 6 | body/tail | T4 | N2 | M1 | — |
| 7 | body/tail | T3 | N1 | M0 | — |
| 8 | body/tail | T4 | N2 | M1 | — |
| 9 | body/tail | T4 | N3 | M1 | — |
| 10 | head | T3 | N1 | M0 | G2 |
| 11 | head | T4 | N1 | M0 | G2 |
| 12 | head | T3 | N0 | M0 | G2 |
| 13 | head | T3 | N1 | M0 | G1 |
| 14 | head | T3 | N1 | M0 | G2 |
| 15 | head | T3 | N0 | M0 | G1 |
| 16 | head | T3 | N1 | M0 | G2 |
| 17 | head | T1 | N0 | M0 | G3 |
| 18 | head | T3 | N1 | M0 | G3 |
| 19 | head | T3 | N1 | M0 | G3 |
| 20 | head | T3 | N1 | M0 | G3 |
| 21 | head | T4 | N2 | M1 | — |
| 22 | head | T3 | N1 | M0 | — |
| 23 | head | T3 | N2 | M1 | — |
| 24 | head | T3 | N2 | M1 | — |
| 25 | head | T2 | N1 | M0 | — |
| 26 | head | T3 | N2 | M1 | — |
| 27 | head | T2 | N1 | M1 | — |
| 28 | head | T2 | N0 | M0 | — |
| 29 | head | T3 | N1 | M0 | — |
| 30 | head | T2 | N0 | M0 | — |
| 31 | head | T2 | N1 | M0 | — |
| 32 | head | T4 | N2 | M1 | — |
| 33 | head | T2 | N1 | M1 | — |
| 34 | head | T3 | N1 | M0 | — |
| 35 | head/body/tail | T4 | N2 | M1 | — |
| 36 | head/tail | T1 | N0 | M0 | G1 |
| 37 | head/uncinate process | T2 | N0 | M0 | — |
| 38 | head/uncinate process | T3 | N2 | M1 | — |
| 39 | head/uncinate process | T2 | N0 | M0 | — |
| 40 | head/uncinate process | T4 | N2 | M1 | — |
| 41 | tail | T4 | N1 | M0 | G3 |
| 42 | tail | T3 | N1 | M0 | G2 |
| 43 | tail | T3 | N0 | M0 | G2 |
| 44 | tail | T4 | N3 | M1 | — |
| 45 | uncinate process | T3 | N1 | M0 | — |
| 46 | uncinate process | T2 | N0 | M0 | — |

TABLE 3E

Clinico-pathological characteristics of glioblastoma patients.

| Patient # | Tumor Origin | Grading |
|---|---|---|
| 1 | primary | G4 |
| 2 | primary | G4 |
| 3 | primary | G4 |
| 4 | primary | G4 |
| 5 | primary | G4 |
| 6 | primary | G4 |
| 7 | primary | G4 |
| 8 | primary | G4 |
| 9 | primary | G4 |
| 10 | primary | G4 |
| 11 | primary | G4 |
| 12 | primary | G4 |
| 13 | primary | G4 |
| 14 | primary | G4 |
| 15 | primary | G4 |
| 16 | primary | G4 |
| 17 | primary | G4 |
| 18 | primary | G4 |
| 19 | primary | G4 |
| 20 | primary | |
| 21 | secondary | G4 |
| 22 | secondary | G4 |
| 23 | secondary | G4 |
| 24 | secondary | G4 |
| 25 | secondary | G4 |
| 26 | secondary | G4 |
| 27 | secondary | G4 |
| 28 | secondary | G4 |
| 29 | secondary | G4 |
| 30 | secondary | |

TABLE 3F

Clinico-pathological characteristics of patients with hematological malignancies.

| Patient # | Hematological disease |
|---|---|
| 1 | ALL |
| 2 | AML |
| 3 | AML |
| 4 | AML |
| 5 | AML |
| 6 | AML |
| 7 | AML |
| 8 | AML |
| 9 | AML |
| 10 | AML |
| 11 | AML |
| 12 | BAL |
| 13 | CML |
| 14 | Hodgkin lymphoma |
| 15 | Hodgkin lymphoma |
| 16 | Hodgkin lymphoma |
| 17 | MDS & MPS |
| 18 | Multiple myeloma |
| 19 | Multiple myeloma |

TABLE 3F-continued

Clinico-pathological characteristics of patients with hematological malignancies.

| Patient # | Hematological disease |
|---|---|
| 20 | Multiple myeloma |
| 21 | MDS |
| 22 | MDS |
| 23 | MDS |
| 24 | MDS |
| 25 | MDS |
| 26 | MDS |
| 27 | MDS |
| 28 | NHL |
| 29 | NHL |
| 30 | NHL |
| 31 | NHL |

Abbreviations:
ALL: Acute Lymphoid Leukemia;
AML: Acute Myeloid Leukemia;
BAL: Biphenotypic Acute Leukemia;
CML: Chronic Myeloid Leukemia;
MDS: Myelodysplastic Syndrome;
MPS: Myeloproliferative Syndrome;
NHL: Non-Hodgkin Lymphoma.

TABLE 4A

Clinico-pathological characteristics of patients with MS (n = 53; 16 males, 37 females).

| Subtype of MS | Numbers |
|---|---|
| Clinico-pathological characteristics of patients with relapsing remitting Multiple Sclerosis (RRMS) | n = 29; 6 males, 23 females |
| Clinico-pathological characteristics of patients with non-relapsing-remitting Multiple Sclerosis (non RRMS) | n = 11; 6 males, 5 females |
| Clinico-pathological characteristics of patients with clinically isolated syndrome (CIS) | n = 13; 4 males, 9 females |

TABLE 4B

Clinico-pathological characteristics of patients with non-inflammatory neurological diseases (NIND). Total n = 21; 7 males, 14 females.

| Symptoms | Numbers |
|---|---|
| Headache | n = 15 |
| Facial pain | n = 1 |
| Pseudo tumor | n = 3 |
| Acute lumboischialgy | n = 2 |

TABLE 4C

Clinico-pathological characteristics of patients with other inflammatory neurological diseases (OIND). Total n = 16; 9 males, 7 females.

| Symptoms | Numbers |
|---|---|
| Encephalitis | n = 11 |
| Meningitis (bacterial viral) | n = 9 |
| Meningoencephalitis | n = 6 |

REFERENCES

1. Lindquist S, Craig E A (1988) The heat-shock proteins. Annu Rev Genet 22: 631-677.
2. Hard F U (1996) Molecular chaperones in cellular protein folding. Nature 381: 571-579.
3. Daugaard M, Rohde M, Jäättelä M (2007) The heat shock protein 70 family: Highly homologous proteins with overlapping and distinct functions. FEBS Lett 581: 3702-3710.
4. De Maio A (1999) Heat shock proteins: facts, thoughts, and dreams. Shock 11: 1-12.
5. Jäättelä M (1999) Escaping cell death: survival proteins in cancer. Exp Cell Res 248: 30-43.
6. Multhoff G, Botzler C, Wiesnet M, Müller E, Meier T, et al. (1995) A stress-inducible 72-kDa heat-shock protein (HSP72) is expressed on the surface of human tumor cells, but not on normal cells. Int J Cancer 61: 272-279.
7. Gehrmann M, Liebisch G, Schmitz G, Anderson R, Steinem C, et al. (2008) Tumor-specific Hsp70 plasma membrane localization is enabled by the glycosphingolipid Gb3. PLoS One 3: e1925.
8. Vega V L, Rodriguez-Silva M, Frey T, Gehrmann M, Diaz J C, et al. (2008) Hsp70 translocates into the plasma membrane after stress and is released into the extracellular environment in a membrane-associated form that activates macrophages. J Immunol 180: 4299-4307.
9. Gehrmann M, Marienhagen J, Eichholtz-Wirth H, Fritz E, Ellwart J, et al. (2005) Dual function of membrane-bound heat shock protein 70 (Hsp70), Bag-4, and Hsp40: protection against radiation-induced effects and target structure for natural killer cells. Cell Death Differ 12: 38-51.
10. Arispe N, Doh M, Simakova O, Kurganov B, De Maio A (2004) Hsc70 and Hsp70 interact with phosphatidylserine on the surface of PC12 cells resulting in a decrease of viability. FASEB J 18: 1636-1645.
11. Botzler C, Li G, Issels R D, Multhoff G (1998) Definition of extracellular localized epitopes of Hsp70 involved in an NK immune response. Cell Stress Chaperones 3: 6-11.
12. Multhoff G, Hightower L E (2011) Distinguishing integral and receptor-bound heat shock protein 70 (Hsp70) on the cell surface by Hsp70-specific antibodies. Cell Stress Chaperones 16: 251-255.
13. Hantschel M, Pfister K, Jordan A, Scholz R, Andreesen R, et al. (2000) Hsp70 plasma membrane expression on primary tumor biopsy material and bone marrow of leukemic patients. Cell Stress Chaperones 5: 438-442.
14. Pfister K, Radons J, Busch R, Tidball J G, Pfeifer M, et al. (2007) Patient survival by Hsp70 membrane phenotype: association with different routes of metastasis. Cancer 110: 926-935.
15. Gastpar R, Gehrmann M, Bausero M A, Asea A, Gross C, et al. (2005) Heat shock protein 70 surface-positive tumor exosomes stimulate migratory and cytolytic activity of natural killer cells. Cancer Res 65: 5238-5247.
16. De Maio A (2011) Extracellular heat shock proteins, cellular export vesicles, and the Stress Observation System: a form of communication during injury, infection, and cell damage. It is never known how far a controversial finding will go! Dedicated to Ferruccio-Ritossa. Cell Stress Chaperones 16: 235-249.
17. Lichtenauer M, Zimmermann M, Nickl S, Lauten A, Goebel B, et al. (2014) Transient hypoxia leads to increased serum levels of heat shock protein-27,-70 and caspase-cleaved cytokeratin 18. Clin Lab 60: 323-328.
18. Lebherz-Eichinger D, Ankersmit H J, Hacker S, Hetz H, Kimberger O, et al. (2012) HSP27 and HSP70 serum and urine levels in patients suffering from chronic kidney disease. Clin Chim Acta 413: 282-286.

19. Fredly H, Reikvam H, Gjertsen B T, Bruserud O (2012) Disease-stabilizing treatment with all-trans retinoic acid and valproic acid in acute myeloid leukemia: serum hsp70 and hsp90 levels and serum cytokine profiles are determined by the disease, patient age, and anti-leukemic treatment. Am J Hematol 87: 368-376.
20. Pockley A G, Shepherd J, Corton J M (1998) Detection of heat shock protein 70 (Hsp70) and anti-Hsp70 antibodies in the serum of normal individuals. Immunol Invest 27: 367-377.
21. Njemini R, Demanet C, Mets T (2005) Comparison of two ELISAs for the determination of Hsp70 in serum. J Immunol Methods 306: 176-182.
22. Bausero M A, Gastpar R, Multhoff G, Asea A (2005) Alternative mechanism by which IFN-gamma enhances tumor recognition: active release of heat shock protein 72. J Immunol 175: 2900-2912.
23. Mathivanan S, Ji H, Simpson R J (2010) Exosomes: extracellular organelles important in intercellular communication. J Proteomics 73: 1907-1920.
24. Théry C, Ostrowski M, Segura E (2009) Membrane vesicles as conveyors of immune responses. Nat Rev Immunol 9: 581-593.
25. Record M, Subra C, Silvente-Poirot S, Poirot M (2011) Exosomes as intercellular signalosomes and pharmacological effectors. Biochem Pharmacol 81: 1171-1182.
26. Anand P K (2010) Exosomal membrane molecules are potent immune response modulators. CommunIntegr Biol 3: 405-408.
27. Kharaziha P, Ceder S, Li Q, Panaretakis T (2012) Tumor cell-derived exosomes: a message in a bottle. Biochim Biophys Acta 1826: 103-111.
28. Botzler C, Schmidt J, Luz A, Jennen L, Issels R, et al. (1998) Differential Hsp70 plasma-membrane expression on primary human tumors and metastases in mice with severe combined immunodeficiency. Int J Cancer 77: 942-948.
29. Stangl S, Gehrmann M, Riegger J, Kuhs K, Riederer I, et al. (2011) Targeting membrane heat-shock protein 70 (Hsp70) on tumors by cmHsp70.1 antibody. Proc Natl Acad Sci USA 108: 733-738.
30. Kahn S E, Watkins B F, Bermes E W Jr (1981) An evaluation of a spectrophotometric scanning technique for measurement of plasma hemoglobin. Ann Clin Lab Sci 11: 126-131.
31. Schilling D, Gehrmann M, Steinem C, De Maio A, Pockley A G, et al. (2009) Binding of heat shock protein 70 to extracellular phosphatidylserine promotes killing of normoxic and hypoxic tumor cells. FASEB J 23: 2467-2477.
32. Armbruster D A, Pry T (2008) Limit of blank, limit of detection and limit of quantitation. Clin Biochem Rev 29 Suppl 1: S49-52.
33. Wenk R E (1998) Mechanism of interference by hemolysis in immunoassays and requirements for sample quality. Clin Chem 44: 2554.
34. Madu C O, Lu Y (2010) Novel diagnostic biomarkers for prostate cancer. J Cancer 1: 150-177.
35. HiralesCasillas C E, Flores Fernández J M, Padilla Camberos E, Herrera López E J, Leal Pacheco G, et al. (2014) Current status of circulating protein biomarkers to aid the early detection of lung cancer. Future Oncol 10: 1501-1513.
36. Alvarez-Chaver P, Otero-Estévez O, Páez de la Cadena M, Rodriguez-Berrocal F J, Martinez-Zorzano V S (2014) Proteomics for discovery of candidate colorectal cancer biomarkers. World J Gastroenterol 20: 3804-3824.
37. Loeb S (2014) Guideline of guidelines: prostate cancer screening. BJU Int 114: 323-325.
38. Grunnet M, Sorensen J B (2012) Carcinoembryonic antigen (CEA) as tumor marker in lung cancer. Lung Cancer 76: 138-143.
39. Hayes J H, Barry M J (2014) Screening for prostate cancer with the prostate-specific antigen test: a review of current evidence. JAMA 311: 1143-1149.
40. Pockley A G, Henderson B, and Multhoff G (in press) Extracellular cell stress proteins as biomarkers of human disease. Biochem Soc Trans
41. Mambula S S, Calderwood S K (2006) Heat shock protein 70 is secreted from tumor cells by a nonclassical pathway involving lysosomal endosomes. J Immunol 177: 7849-7857.
42. Broquet A H, Thomas G, Masliah J, Trugnan G, Bachelet M (2003) Expression of the molecular chaperone Hsp70 in detergent-resistant microdomains correlates with its membrane delivery and release. J Biol Chem 278: 21601-21606.
43. Schildkopf P, Frey B, Ott O J, Rubner Y, Multhoff G, et al. (2011) Radiation combined with hyperthermia induces HSP70-dependent maturation of dendritic cells and release of pro-inflammatory cytokines by dendritic cells and macrophages. Radiother Oncol 101: 109-115.
44. Brown D A, London E (2000) Structure and function of sphingolipid- and cholesterol-rich membrane rafts. J Biol Chem 275: 17221-17224.

The invention claimed is:

1. A method of evaluating tumor disease therapy in a human subject having cancer, comprising:
   (a) obtaining a serum or plasma sample from the subject before treatment, wherein the serum or plasma is separated from blood by centrifugation to obtain serum or plasma free of viable tumor cells;
   (b) detecting a higher concentration of free and tumor derived exosomal heat shock protein 70 (Hsp70) in the sample from the subject having cancer as compared to a median concentration of 7.7 ng/mL obtained from healthy subjects, wherein the concentration of free and tumor derived exosomal heat shock protein 70 (Hsp70) is detected by performing a sandwich ELISA comprising:
   (i) contacting the sample of (a), with a capture polyclonal anti-HSP 70 antibody and a detection monoclonal anti-HSP 70 antibody, selected from the group consisting of: antibody cmHsp70.1 produced by hybridoma cmHsp70.1 (Accession Number DSM ACC2629) and antibody cmHsp70.2 produced by hybridoma cmHsp70.2 (Accession Number DSM ACC2630),
   (ii) detecting binding between free and tumor derived exosomal heat shock protein 70 (Hsp70) in the sample of (a) and the antibodies of (i), and
   (iii) quantifying the free and tumor derived exosomal heat shock protein 70 (Hsp70) using an eight point standard of 0-50 ng/ml recombinant Hsp70;
   (c) administering an anti-tumor treatment wherein the anti-tumor treatment is selected from the group consisting of radiation, surgery and chemotherapy; and
   (d) monitoring the concentration of free and tumor derived exosomal heat shock protein 70 (Hsp70) in a serum or plasma sample following administration of the anti-tumor agent by performing the sandwich ELISA, wherein a reduced level of free and tumor derived exosomal Hsp70 following administration of the anti-tumor agent as compared to the level in the sample of (a), indicates progress in the treatment and therapeutic utility of the anti-tumor agent, wherein the tumor is selected from the group consisting of head and neck cancer, lung cancer, colorectal carcinoma, pancreatic cancer, glioblastoma, and a hematological malignancy.

2. The method of claim 1, wherein the detection monoclonal anti-HSP 70 antibody comprises a detectable label selected from the group consisting of an enzyme, a radioisotope, a fluorophore, a heavy metal, a tag, and a ligand.

3. The method of claim 1, wherein the detection monoclonal anti-HSP 70 antibody is biotinylated.

4. The method of claim 1, wherein the subject has a serum or plasma sample Hsp70 level greater than 10 ng/ml before administration of the anti-tumor agent.

5. The method of claim 1, wherein the serum or plasma in the sample is diluted in buffer.

6. The method of claim 1, wherein the serum or plasma in the sample is diluted 1:5 in buffer prior to the assay.

* * * * *